(12) United States Patent
Cheng et al.

(10) Patent No.: US 10,035,700 B2
(45) Date of Patent: *Jul. 31, 2018

(54) SEMICONDUCTOR STRUCTURE AND MANUFACTURING METHOD THEREOF

(71) Applicant: TAIWAN SEMICONDUCTOR MANUFACTURING COMPANY LTD., Hsinchu (TW)

(72) Inventors: Chun-Wen Cheng, Hsinchu County (TW); Chia-Hua Chu, Hsinchu County (TW); Fei-Lung Lai, New Taipei (TW); Shiang-Chi Lin, Taoyuan (TW)

(73) Assignee: TAIWAN SEMICONDUCTOR MANUFACTURING COMPANY LTD., Hsinchu (TW)

(*) Notice: Subject to any disclaimer, the term of this patent is extended or adjusted under 35 U.S.C. 154(b) by 0 days.

This patent is subject to a terminal disclaimer.

(21) Appl. No.: 15/416,411

(22) Filed: Jan. 26, 2017

(65) Prior Publication Data

US 2017/0129771 A1    May 11, 2017

Related U.S. Application Data

(63) Continuation of application No. 14/844,486, filed on Sep. 3, 2015, now Pat. No. 9,567,209.

(51) Int. Cl.
*B81C 1/00* (2006.01)
*B81B 3/00* (2006.01)
*B81B 7/00* (2006.01)
*G01N 27/12* (2006.01)

(52) U.S. Cl.
CPC ............ *B81B 7/007* (2013.01); *B81C 1/0015* (2013.01); *B81C 1/00158* (2013.01); *B81C 1/00182* (2013.01); *B81C 1/00301* (2013.01); *G01N 27/123* (2013.01); *B81B 2201/0214* (2013.01); *B81B 2203/0127* (2013.01); *B81B 2203/0315* (2013.01); *B81B 2203/04* (2013.01); *B81B 2207/012* (2013.01); *B81B 2207/07* (2013.01); *B81C 2203/035* (2013.01); *B81C 2203/0792* (2013.01)

(58) Field of Classification Search
None
See application file for complete search history.

(56) References Cited

U.S. PATENT DOCUMENTS

| | | |
|---|---|---|
| 8,987,059 B2 | 3/2015 | Liang et al. |
| 9,040,334 B2 | 5/2015 | Chu et al. |
| 9,065,358 B2 | 6/2015 | Tsai et al. |
| 9,085,455 B2 | 7/2015 | Cheng et al. |
| 9,085,456 B2 | 7/2015 | Tsai et al. |
| 9,122,827 B2 | 9/2015 | Chen et al. |
| 9,133,017 B2 | 9/2015 | Liang et al. |

(Continued)

*Primary Examiner* — Minh-Loan Tran
(74) *Attorney, Agent, or Firm* — WPAT, P.C., Intellectual Property Attorneys; Anthony King

(57) ABSTRACT

A semiconductor structure includes a substrate including a plurality of vias passing through the substrate and filled with a conductive or semiconductive material, and an oxide layer surrounding the conductive or semiconductive material, the substrate defining a cavity therein; a membrane disposed over the substrate and the cavity; a heater disposed within the membrane and electrically connected with the substrate; and a sensing electrode disposed over the membrane and the heater.

20 Claims, 30 Drawing Sheets

(56) References Cited

U.S. PATENT DOCUMENTS

| | | |
|---|---|---|
| 9,138,994 B2 | 9/2015 | Peng et al. |
| 9,139,420 B2 | 9/2015 | Chang et al. |
| 9,139,423 B2 | 9/2015 | Chien et al. |
| 9,181,083 B2 | 11/2015 | Tsai et al. |
| 9,187,317 B2 | 11/2015 | Cheng et al. |
| 9,233,839 B2 | 1/2016 | Liu et al. |
| 9,236,877 B2 | 1/2016 | Peng et al. |
| 9,238,581 B2 | 1/2016 | Wu et al. |
| 9,567,209 B1 * | 2/2017 | Cheng .................... G01L 9/0041 |
| 2012/0074554 A1 * | 3/2012 | Cheng ................. B81C 1/00269 257/684 |
| 2013/0313675 A1 * | 11/2013 | Nakano ................... G01F 1/692 257/467 |
| 2014/0252508 A1 * | 9/2014 | Cheng ................. B81C 1/00246 257/415 |
| 2014/0287548 A1 | 9/2014 | Lin et al. |
| 2015/0137303 A1 | 5/2015 | Chou et al. |
| 2015/0175405 A1 | 6/2015 | Cheng |
| 2015/0175407 A1 | 6/2015 | Cheng et al. |
| 2015/0196912 A1 | 7/2015 | Tsai et al. |
| 2015/0251895 A1 * | 9/2015 | Chu .................... B81C 1/00238 257/595 |

* cited by examiner

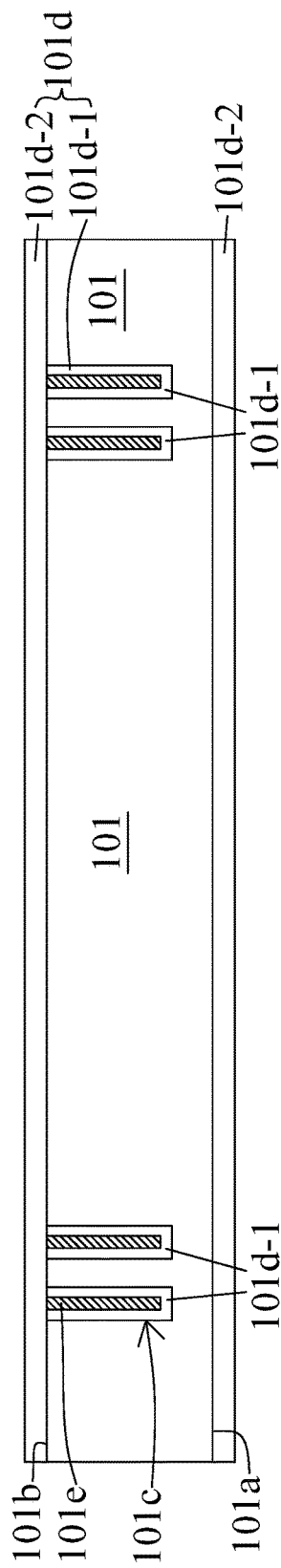
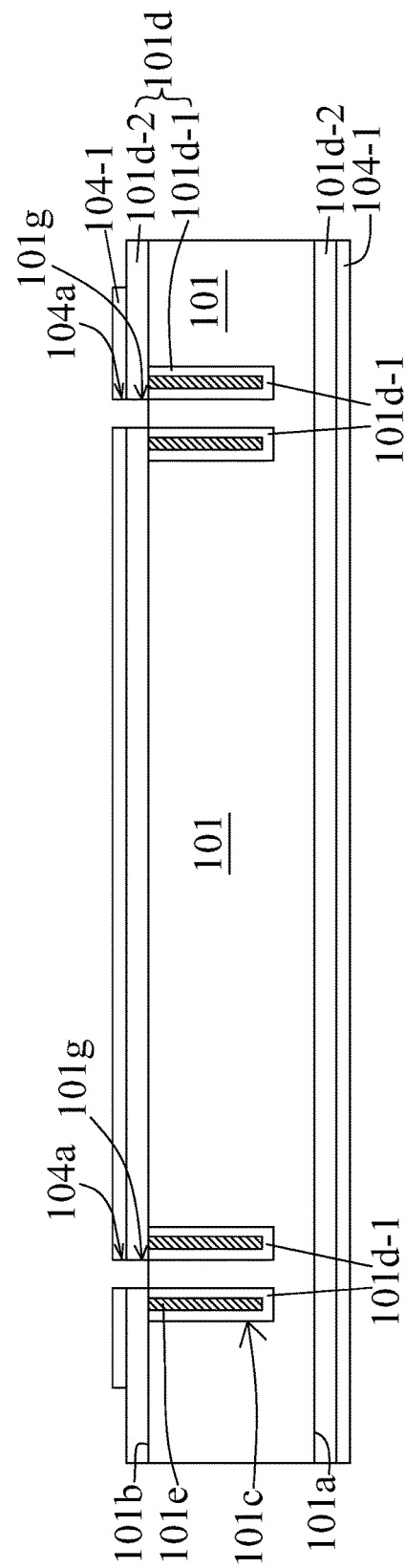
FIG. 9A
FIG. 9B

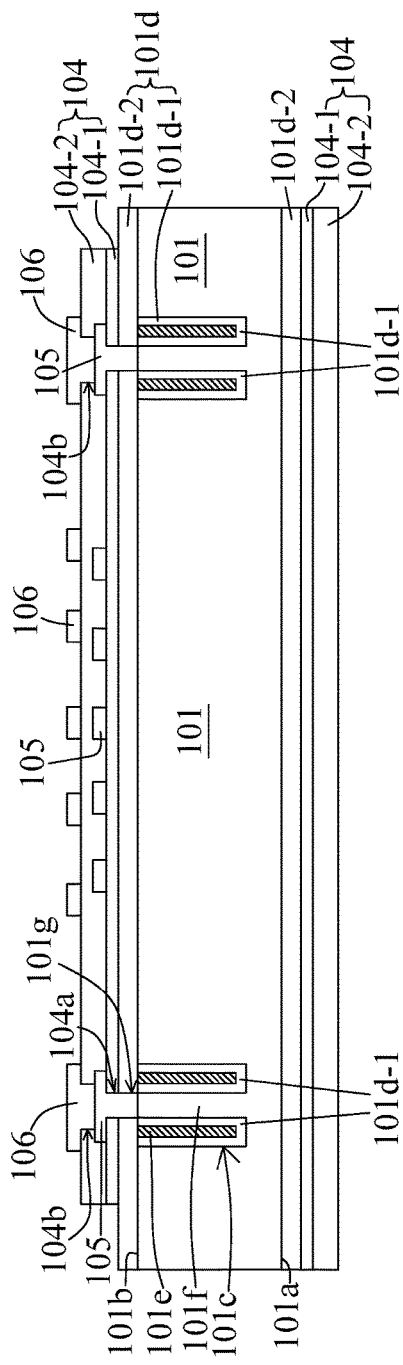
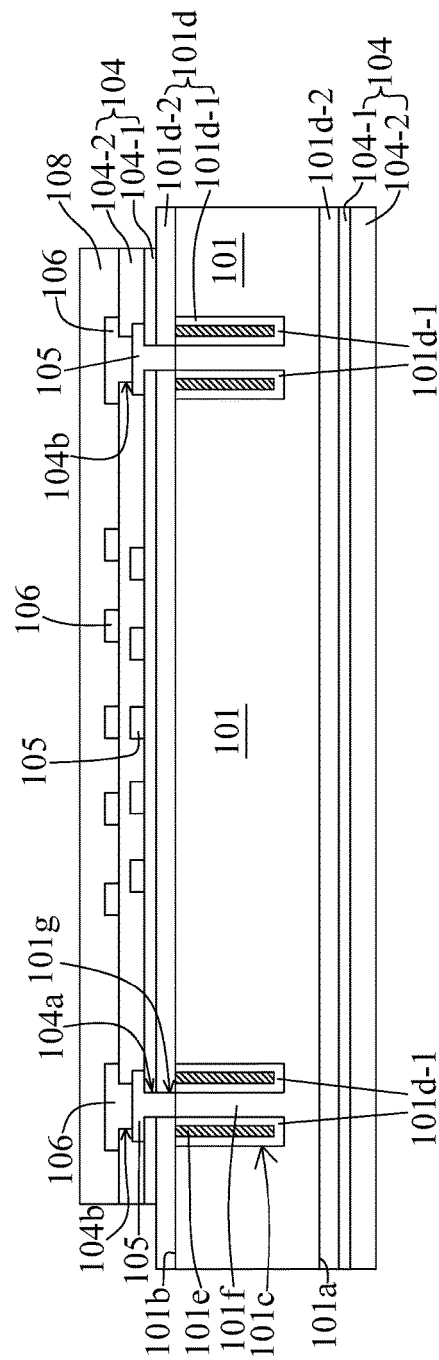
FIG. 9E
FIG. 9F

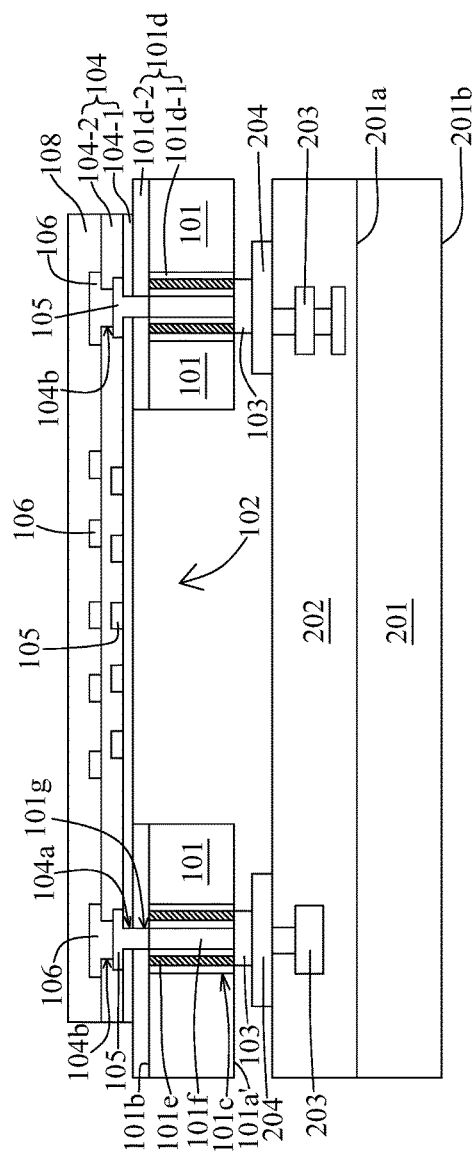
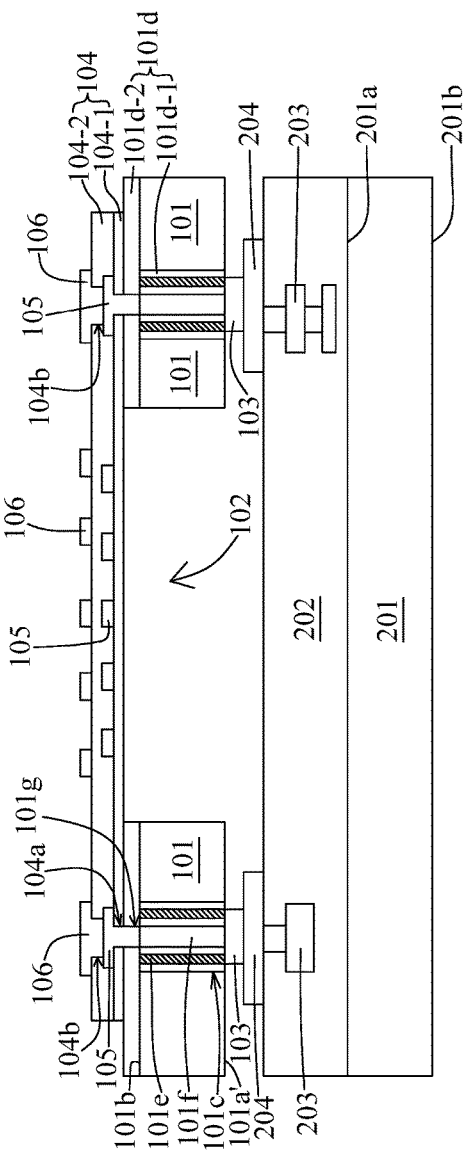
FIG. 9K
FIG. 9L

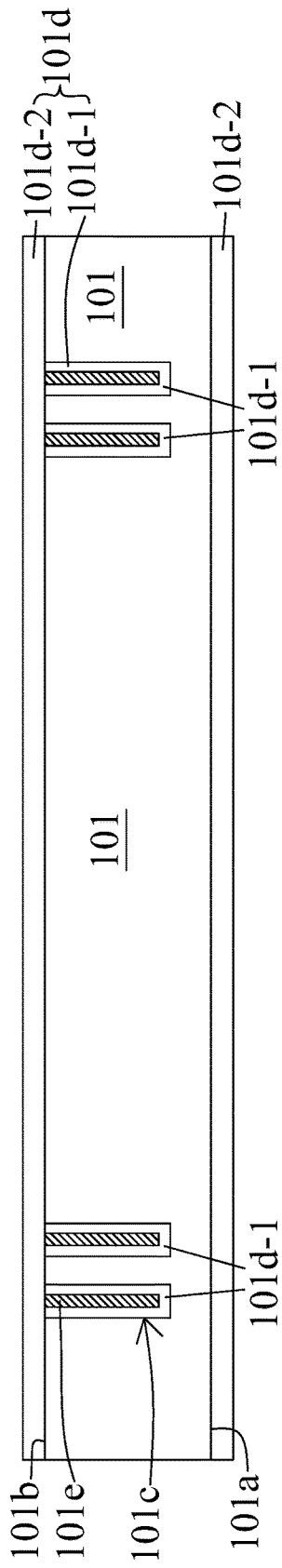
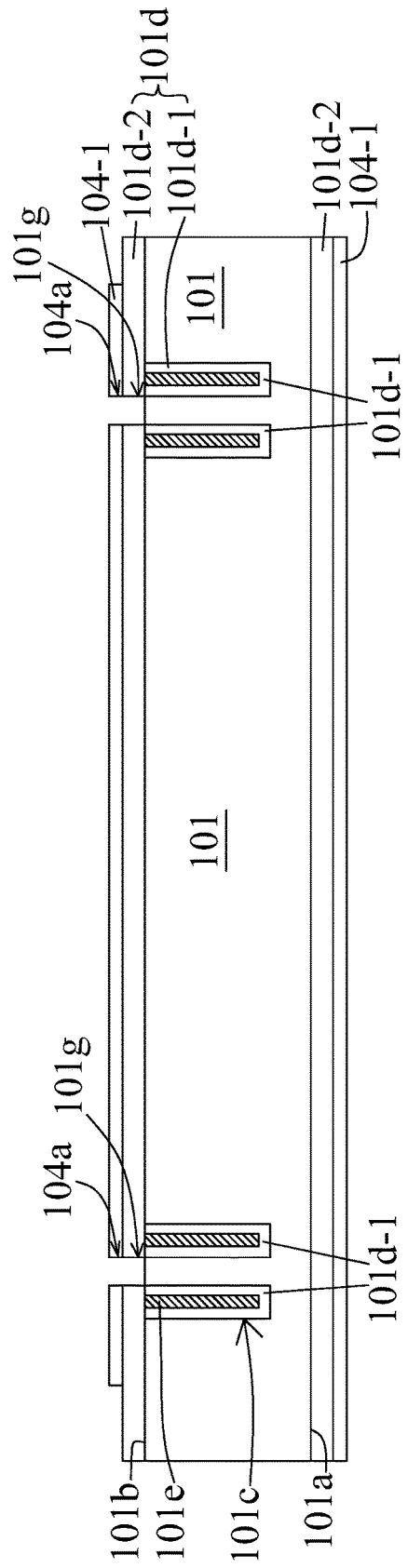
FIG. 10A
FIG. 10B

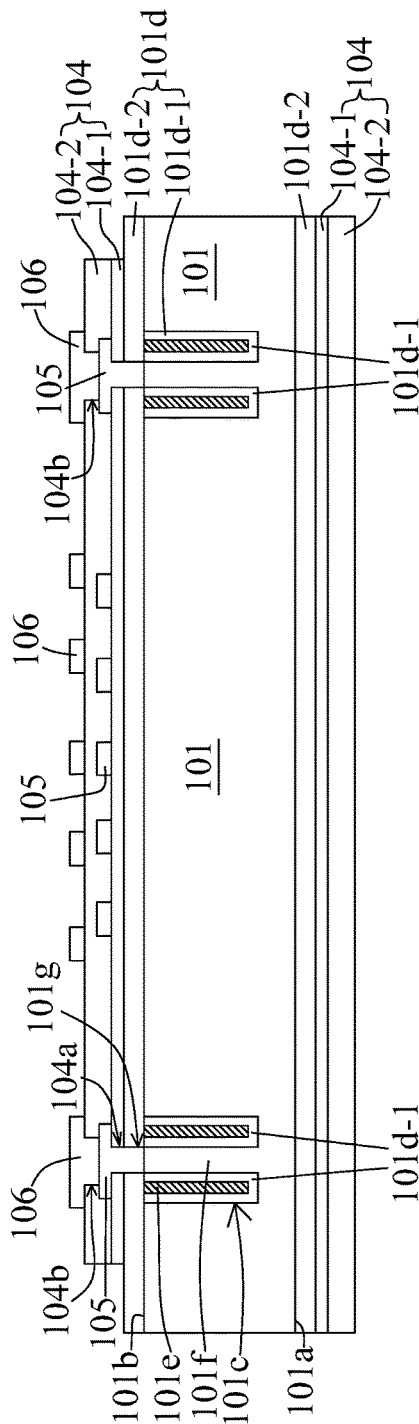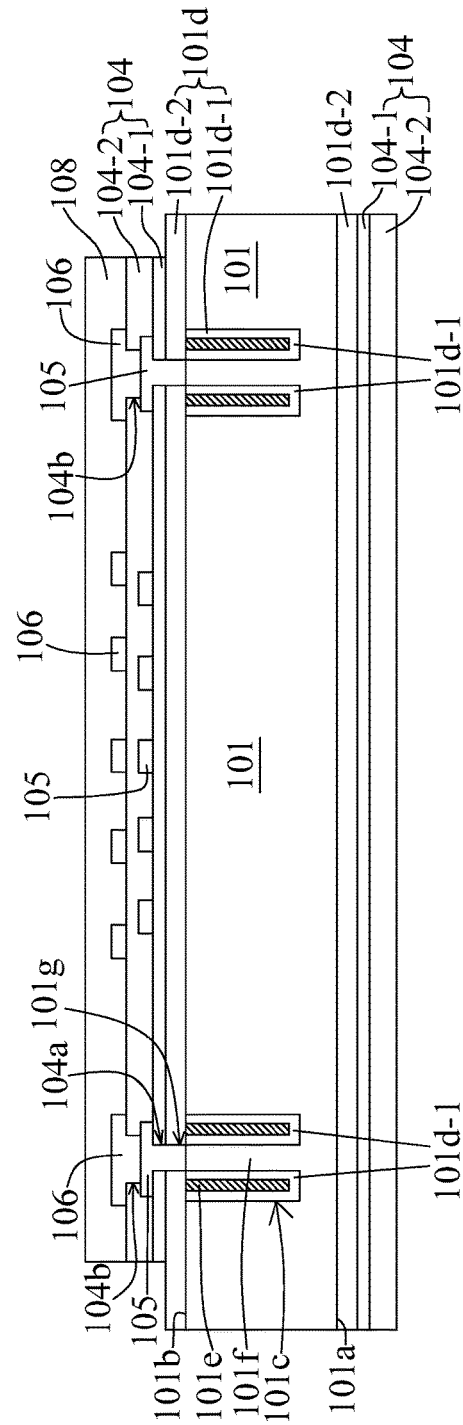
FIG. 10E
FIG. 10F

SEMICONDUCTOR STRUCTURE AND MANUFACTURING METHOD THEREOF

PRIORITY CLAIM AND CROSS-REFERENCE

This application claims priority to U.S. application Ser. No. 14/844,486, filed on Sep. 3, 2015, entitled "Semiconductor Structure and Manufacturing Method Thereof," which application is hereby incorporated herein by reference.

BACKGROUND

Electronic equipment involving semiconductive devices are essential for many modern applications. The semiconductive device has experienced rapid growth. Technological advances in materials and design have produced generations of semiconductive devices where each generation has smaller and more complex circuits than the previous generation. In the course of advancement and innovation, functional density (i.e., the number of interconnected devices per chip area) has generally increased while geometric size (i.e., the smallest component that can be created using a fabrication process) has decreased. Such advances have increased the complexity of processing and manufacturing semiconductive devices.

Micro-electro mechanical system (MEMS) devices have been recently developed and are also commonly involved in electronic equipment. The MEMS device is micro-sized device, usually in a range from less than 1 micron to several millimeters in size. The MEMS device includes fabrication using semiconductive materials to form mechanical and electrical features. The MEMS device may include a number of elements (e.g., stationary or movable elements) for achieving electro-mechanical functionality. MEMS devices are widely used in various applications. MEMS applications include motion sensors, pressure sensors, printer nozzles, or the like. Other MEMS applications include inertial sensors, such as accelerometers for measuring linear acceleration and gyroscopes for measuring angular velocity. Moreover, MEMS applications are extended to optical applications, such as movable mirrors, and radio frequency (RF) applications, such as RF switches or the like.

As technologies evolve, design of the devices becomes more complicated in view of small dimension as a whole and increase of functionality and amounts of circuitries. The devices involve many complicated steps and increases complexity of manufacturing. The increase in complexity of manufacturing may cause deficiencies such as high yield loss, warpage, low signal to noise ratio (SNR), etc. Therefore, there is a continuous need to modify structure and manufacturing method of the devices in the electronic equipment in order to improve the device performance as well as reduce manufacturing cost and processing time.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 9A is a cross-sectional view of a first substrate in accordance with some embodiments of the present disclosure.

FIG. 9B is a cross-sectional view of a first substrate with a first membrane layer in accordance with some embodiments of the present disclosure.

FIG. 9E is a cross-sectional view of a first substrate with a sensing electrode in accordance with some embodiments of the present disclosure.

FIG. 9F is a cross-sectional view of a first substrate with a sacrificial oxide in accordance with some embodiments of the present disclosure.

FIG. 9K is a cross-sectional view of a first substrate bonded with a second substrate in accordance with some embodiments of the present disclosure.

FIG. 9L is a cross-sectional view of removal of a sacrificial oxide in accordance with some embodiments of the present disclosure.

FIG. 10A is a cross-sectional view of a first substrate in accordance with some embodiments of the present disclosure.

FIG. 10B is a cross-sectional view of a first substrate with a first membrane layer in accordance with some embodiments of the present disclosure.

FIG. 10E is a cross-sectional view of a first substrate with a sensing electrode in accordance with some embodiments of the present disclosure.

FIG. 10F is a cross-sectional view of a first substrate with a sacrificial oxide in accordance with some embodiments of the present disclosure.

FIGS. 10L-1 and 10L-2 are cross-sectional views of a second substrate with an isolation layer in accordance with some embodiments of the present disclosure.

DETAILED DESCRIPTION OF THE DISCLOSURE

Figure 1:
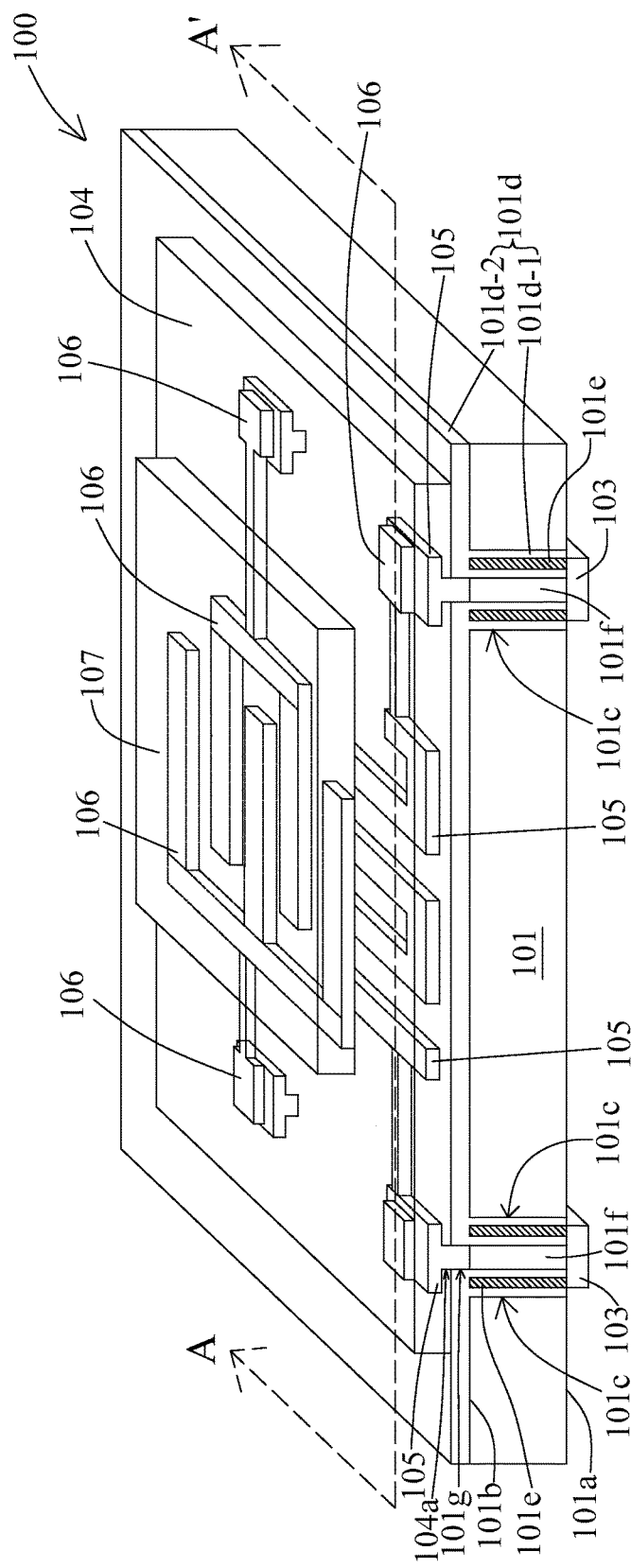
FIG. 1 is a schematic perspective view of a semiconductor structure in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

A sensor is an electronic equipment for detecting a present of a predetermined material such as a liquid, a gas or etc. The sensor can sense the present of the predetermined material by various suitable mechanisms such as electrochemical, electromechanical, optical or etc. The sensor can sense the predetermined material and generate an electrical signal accordingly for further processing. The sensor can involve a MEMS device for sensing the present of the predetermined material by electromechanical mechanism, and a complementary metal oxide semiconductor (CMOS) device for processing the electrical signal generated upon the detection of the present of the predetermined material. The MEMS device can integrate with the CMOS device by suitable operations such as wire bonding. Since the sensor involves the MEMS device and the CMOS device which are fabricated separately, a geometric size or a form factor of the sensor is undesirably large.

Furthermore, the sensor is required to be operated under a predetermined high operating temperature (for example, greater than 700° C.). The sensor includes a heater for providing the predetermined operating temperature for sensing the predetermined material. The heater is made of various materials such as tungsten. However, a heating efficiency of the heater made by tungsten is relatively low, and a power consumption of the heater is undesirably high.

In the present disclosure, a sensor with an improved semiconductor structure is disclosed. The semiconductor structure includes a MEMS device and a CMOS device. The MEMS device and the CMOS device are integrated by formation of vias and bonding operations. Several vias are formed in a MEMS substrate, and a metallic material is disposed over a surface of the MEMS substrate. The metallic material is configured to be bonded with a bonding structure disposed over the CMOS substrate. As such, the MEMS device is integrated with the CMOS device by the metallic material and the bonding structure. Such integration can reduce a form factor of the semiconductor structure and miniaturize the sensor. Furthermore, a performance of the sensor with the improved semiconductor structure is enhanced, such as low parasitic capacitance, low noise, high signal to noise ratio (SNR), high sensitivity and reactivity, etc.

In addition, the MEMS device in the semiconductor structure is configured to detect a present of a predetermined gas. The MEMS device includes a membrane, a heater, a sensing electrode and a sensing material. The sensing electrode can detect the predetermined gas and generate a corresponding electrical signal when the predetermined gas is present and reacted with the sensing material. The MEMS device is required to operate for detection of the predetermined gas under a predetermined temperature. The heater provides the predetermined temperature for the operation of the MEMS device. The heater includes tungsten alloy, tungsten silicide (WSi), titanium tungsten (TiW), titanium aluminum nitride (TiAlN), tantalum aluminum (TaAl) or etc. Such heater has a high resistivity and thus provides a high heating efficiency during the operation of the MEMS device.

Figure 2:
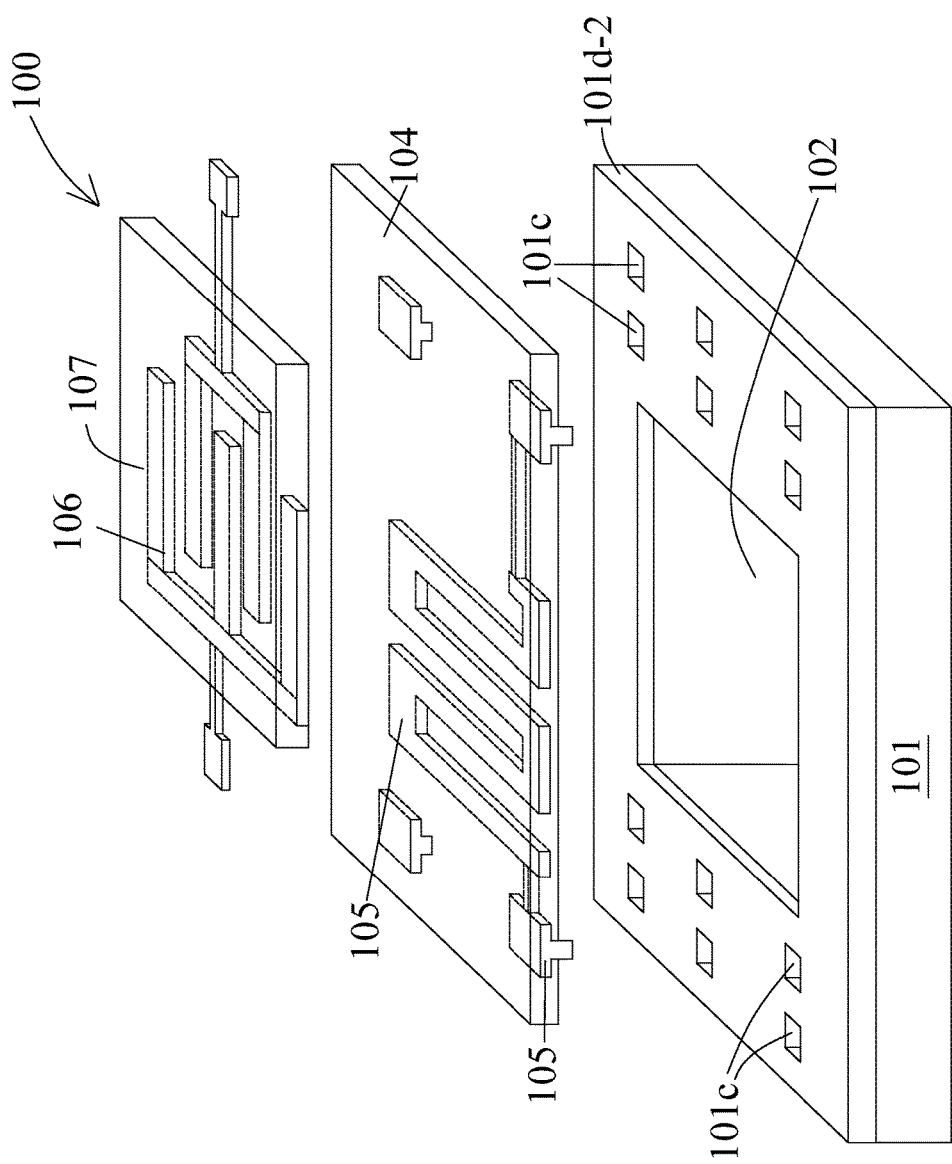
FIG. 2 is a schematic exploded view of a semiconductor structure of FIG. 1 in accordance with some embodiments of the present disclosure.
Figure 3:
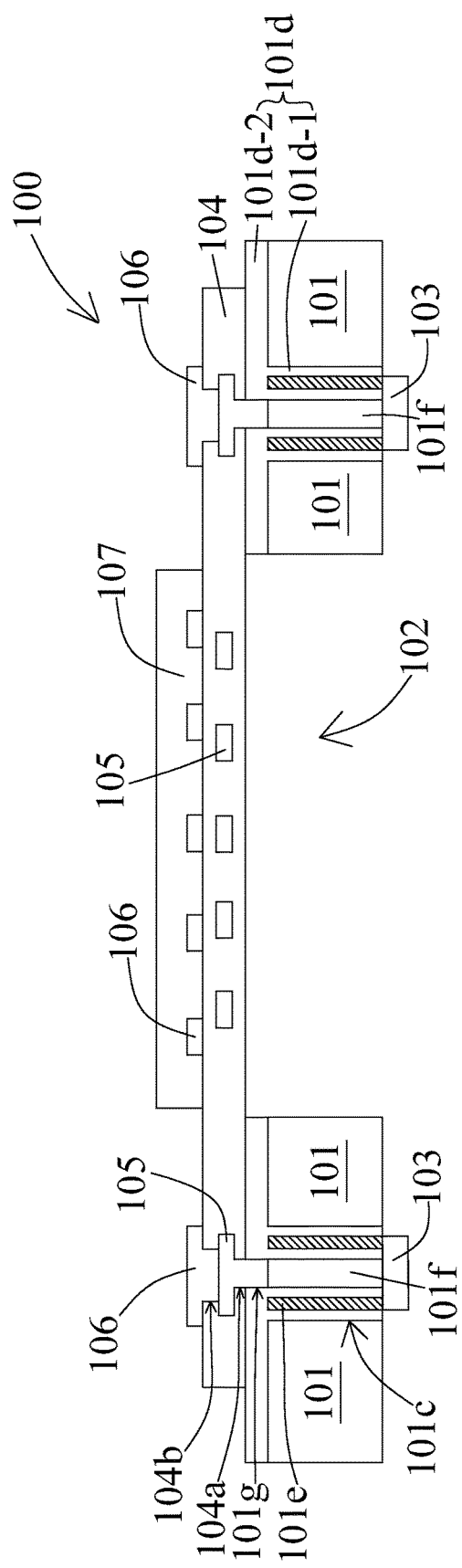
FIG. 3 is a schematic cross-sectional view of a semiconductor structure along AA' of FIG. 1 in accordance with some embodiments of the present disclosure.

FIG. 1 is a schematic perspective view of a semiconductor structure accordance with some embodiments of the present disclosure. The semiconductor structure includes a first device 100. The first device 100 includes a first substrate 101, an oxide 101d, a cavity 102, a metallic material 103, a membrane 104, a heater 105, a sensing electrode 106 and a sensing material 107. FIG. 2 is a schematic exploded view of the first device 100, which illustrates the first substrate 101, the membrane 104 and the sensing material 107. The heater 105 is disposed inside the membrane 104. The sensing electrode 106 is partially covered by the sensing material 107. FIG. 3 is a schematic cross sectional view of the first device 100 along AA' of FIG. 1.

In some embodiments, the first device 100 is configured to sense a present of a predetermined material such as a gas. In some embodiment, the first device 100 is configured to detect a present of a toxic and hazardous gas such as carbon monoxide, etc. In some embodiments, the first device 100 is a part of a sensor. In some embodiments, the first device 100 is a part of a gas sensor or a gas detector. In some embodiments, the first device 100 can generate an electrical signal when the predetermined material is present and detected. In some embodiments, the first device 100 is a MEMS device including electro-mechanical elements. In some embodiments, the first device 100 has a small form factor. In some embodiments, the first device 100 has a thickness of about less than about 100 um. In some embodiments, the first device 100 is configured to be disposed over and bonded with another substrate.

In some embodiments, the first device 100 includes the first substrate 101. In some embodiments, the first substrate 101 includes silicon, glass, ceramic or other suitable materials. In some embodiments, the first substrate 101 is a silicon substrate. In some embodiments, the first substrate 101 is a MEMS substrate. In some embodiments, the first substrate 101 includes electrical circuits formed on or in the first substrate 101. In some embodiments, the first substrate 101 includes transistors, capacitors, resistors, diodes, photodiodes and/or the like. In some embodiments, the first substrate 101 has a thickness of about 20 um to about 500 um.

In some embodiments, the first substrate 101 includes a first surface 101a, a second surface 101b opposite to the first surface 101a. In some embodiments, the first substrate 101 includes several vias 101c passing through the first substrate 101. In some embodiments, each via 101c is extended from the first surface 101a to the second surface 101b. In some embodiments, the vias 101c are trenches. In some embodiments, there is a portion 101f of the first substrate 101 surrounded by adjacent vias 101c. The portion 101f is disposed between two or more of the vias 101c. In some embodiments, each via 101c is filled with a conductive or semiconductive material 101e. In some embodiments, the conductive or semiconductive material 101e includes poly silicon. In some embodiments, the conductive or semiconductive material 101e is isolated from the first substrate 101 by the first oxide layer 101d-1. In some embodiments, the portion 101f of the first substrate 101 is surrounded by the first oxide layer 101d-1 and the conductive or semiconductive material 101e.

In some embodiments, the first substrate 101 includes a first oxide layer 101d-1 disposed within the first substrate 101. In some embodiments, the first oxide layer 101d-1 is disposed conformal to the vias 101c. In some embodiments, the first oxide layer 101d-1 is disposed over a sidewall of the via 101c. In some embodiments, the first oxide layer 101d-1 surrounds the conductive or semiconductive material 101e. In some embodiments, the first oxide layer 101d-1 isolates the portion 101f and the conductive or semiconductive material 101e from a rest of the first substrate 101. In some embodiments, the first oxide layer 101d-1 includes silicon oxide or any other suitable materials. In some embodiments, the first oxide layer 101d-1 has a thickness of about 0.1 um to about 5 um.

In some embodiments, a second oxide layer 101d-2 is disposed over the second surface 101b of the first substrate 101 and the vias 101c. In some embodiments, the second oxide layer 101d-2 covers the second surface 101b, a portion of the first oxide layer 101d-1 and a portion of the conductive or semiconductive material 101e. In some embodiments, the second oxide layer 101d-2 has a thickness of about 0.1 um to about 5 um. In some embodiments, the second oxide layer 101d-2 is configured to promote an adhesion with a structure or material disposed thereon.

In some embodiments, the second oxide layer 101d-2 includes several first recesses 101g. In some embodiments, the first recess 101g exposes a part of the portion 101f of the first substrate 101. In some embodiments, the portion 101f of the first substrate 101 is not covered by the second oxide layer 101d-2. In some embodiments, the second oxide layer 101d-2 is coupled with the first oxide layer 101d-1 and becomes the oxide 101d. In some embodiments, the second oxide layer 101d-2 includes same material as or different material from the first oxide layer 101d-1. In some embodiments, the second oxide layer 101d-2 includes silicon oxide or other suitable materials. In some embodiments, the thickness of the second oxide layer 101d-2 is same or different from the thickness of the first oxide layer 101d-1.

In some embodiments, the cavity 102 is disposed within the first substrate 101. In some embodiments, the cavity 102 is surrounded by the first substrate 101. In some embodiments, the cavity 102 passes through the first substrate 101 and the second oxide layer 101d-2. In some embodiments, the cavity 102 extends through the first surface 101a and the second surface 101b of the first substrate 101. In some embodiments, the second oxide layer 101d-2 is disposed over the cavity 102. The cavity 102 passes through the first substrate 101 but not the second oxide layer 101d-2. In some embodiments, the cavity 102 is disposed at a central portion of the first substrate 101. In some embodiments, a cross section of the cavity 102 is in a rectangular, quadrilateral, triangular, circular, polygonal or other suitable shapes.

In some embodiments, the metallic material 103 is disposed over the first surface 101a of the first substrate 101. In some embodiments, the metallic material 103 covers the portion 101f of the first substrate 101 or the vias 101c. In some embodiments, the metallic material 103 is electrically connected with the portion 101f of the first substrate 101 or the conductive or semiconductive material 101e. In some embodiments, the metallic material 103 includes copper, aluminum, aluminum copper alloy or other suitable materials. In some embodiments, the metallic material 103 is configured to electrically connect with a circuitry external to the first substrate 101. In some embodiments, the metallic material 103 is configured to receive a bonding structure.

In some embodiments, the membrane 104 is disposed over the second surface 101b of the first substrate 101, the second oxide layer 101d-2 and the cavity 102. In some embodiments, the membrane 104 is attached with the second oxide layer 101d-2. In some embodiments, the membrane 104 includes several holes through the membrane 104. In some embodiments, the membrane 104 includes silicon, silicon dioxide, silicon nitride, silicon carbide, porous silicon, composite film or other suitable materials. In some embodiments, the membrane 104 has a low conductivity to minimize heat loss. The heat provided by the heater 105 would not be easily dissipated by the membrane 104. In some embodiments, the membrane 104 is in a rectangular, quadrilateral, triangular, circular, polygonal or any other suitable shapes. In some embodiments, the membrane 104 has a thickness of about 0.1 um to about 10 um.

In some embodiments, the heater 105 is disposed within the membrane 104. In some embodiments, the heater 105 includes single or multiple layers. The layers are disposed over each other. In some embodiments, the heater 105 includes tungsten alloy, tungsten silicide (WSi), titanium tungsten (TiW), titanium aluminum nitride (TiAlN), tantalum aluminum (TaAl), chromium (Cr), platinum (Pt), titanium nitride (TiN), molybdenum (Mo), polysilicon, silicon carbide (SiC), tantalum nitride (TaN), tantalum oxide (TaO) or other suitable materials. In some embodiments, the heater 105 has a width of about 0.1 um to about 25 um. In some embodiments, a melting point of the heater 105 is about 500° C.-3000° C. In some embodiments, a resistivity of the heater 105 is greater than about $6 \times 10^{-8}$ ohm-meter ($\Omega \cdot m$).

In some embodiments, the heater 105 is configured to provide an operating temperature for sensing a predetermined material by the first device 100. A present of the predetermined material is sensed under the operating temperature. In some embodiments, the operating temperature is about 200° C. to about 800° C. In some embodiments, the operating temperature is greater than about 500° C. In some embodiments, a portion of the heater 105 is electrically connected to a power source, such that the heater 105 can provide the operating temperature when an electric current supplied from the power source passes through the heater 105.

In some embodiments, the heater 105 is laterally extended across the membrane 104. In some embodiments, the heater 105 is extended vertically along the membrane 104. In some embodiments, the heater 105 is in a zigzag configuration. In some embodiments, the heater 105 is extended over and across the cavity 102. In some embodiments, the heater 105 is electrically connected with the first substrate 101. In some embodiments, a portion of the heater 105 is electrically connected with the portion 101f of the first substrate 101 through the first recess 101g. In some embodiments, the portion of the heater 105 is extended from the membrane 104 to the portion 101f of the first substrate 101 through the second oxide layer 101d-2. As such, the portion of the heater 105 is surrounded by the membrane 104, the second oxide layer 101d-2 and the portion 101f of the first substrate 101.

In some embodiments, the sensing electrode 106 is disposed over the membrane 104 and the heater 105. In some embodiments, the sensing electrode 106 includes tungsten alloy, titanium tungsten (TiW), titanium aluminum nitride (TiAlN), tantalum aluminum (TaAl), titanium, titanium nitride (TiN), tantalum, tantalum nitride (TaN), tantalum oxide (TaO), tantalum silicon nitride (TaSiN), platinum (Pt) or other suitable materials. In some embodiments, the sensing electrode 106 is configured to sense a predetermined material such as a gas. When the predetermined material is present, the sensing electrode 106 would generate and transmit an electrical signal to the first substrate 101, other external substrate or other device for further processing. In some embodiments, the sensing electrode 106 has a width of about 0.1 um to about 25 um.

In some embodiments, the sensing electrode 106 is extended laterally or vertically over a surface of the membrane 104. In some embodiments, the sensing electrode 106 is laterally extended across the surface of the membrane 104. In some embodiments, the sensing electrode 106 is in a comb structure. In some embodiments, a portion of the sensing electrode 106 is coupled with the portion of the heater 105 through a third recess 104b of the membrane 104. The portion of the sensing electrode 106 is extended through the third recess 104b towards the heater 105.

In some embodiments, the sensing material 107 is disposed over the cavity 102 and contacts with the sensing electrode 106. In some embodiments, the sensing material 107 partially covers the sensing electrode 106, such that a portion of the sensing electrode 106 is encapsulated by the sensing material 107 while another portion of the sensing electrode 106 is extended out from the sensing material 107. In some embodiments, the sensing material includes tin dioxide ($SnO_2$), zinc oxide (ZnO), indium oxide ($In_2O_3$) or other suitable materials.

In some embodiments, the sensing material 107 is configured to detect a predetermined material under the operating temperature. In some embodiment, a resistance of the sensing material 107 would change when the predetermined material is present and contacted with the sensing material 107. In some embodiments, the sensing electrode 106 is configured to sense a change of resistance of the sensing material 107. The resistance of the sensing material 107 is varied by a chemical reaction between the sensing material 107 and the predetermined material. The sensing material 107 would react with the predetermined material, resulting in a change of the resistance of the sensing material 107. For example, when the predetermined material such as carbon monoxide is present, the resistance of the sensing material 107 would be significantly dropped. The decrease of the resistance would initiate generation of an electrical signal from the sensing electrode 106. The electrical signal would transmit to the first substrate 101 or other substrate/device accordingly for further processing, such that the present of the predetermined material is detected. In some embodiments, when the predetermined material is present, an electrical signal would be generated and transmitted from the sensing electrode 106 to the metallic material 103 through the portion 101f of the first substrate 101.

Figure 4:
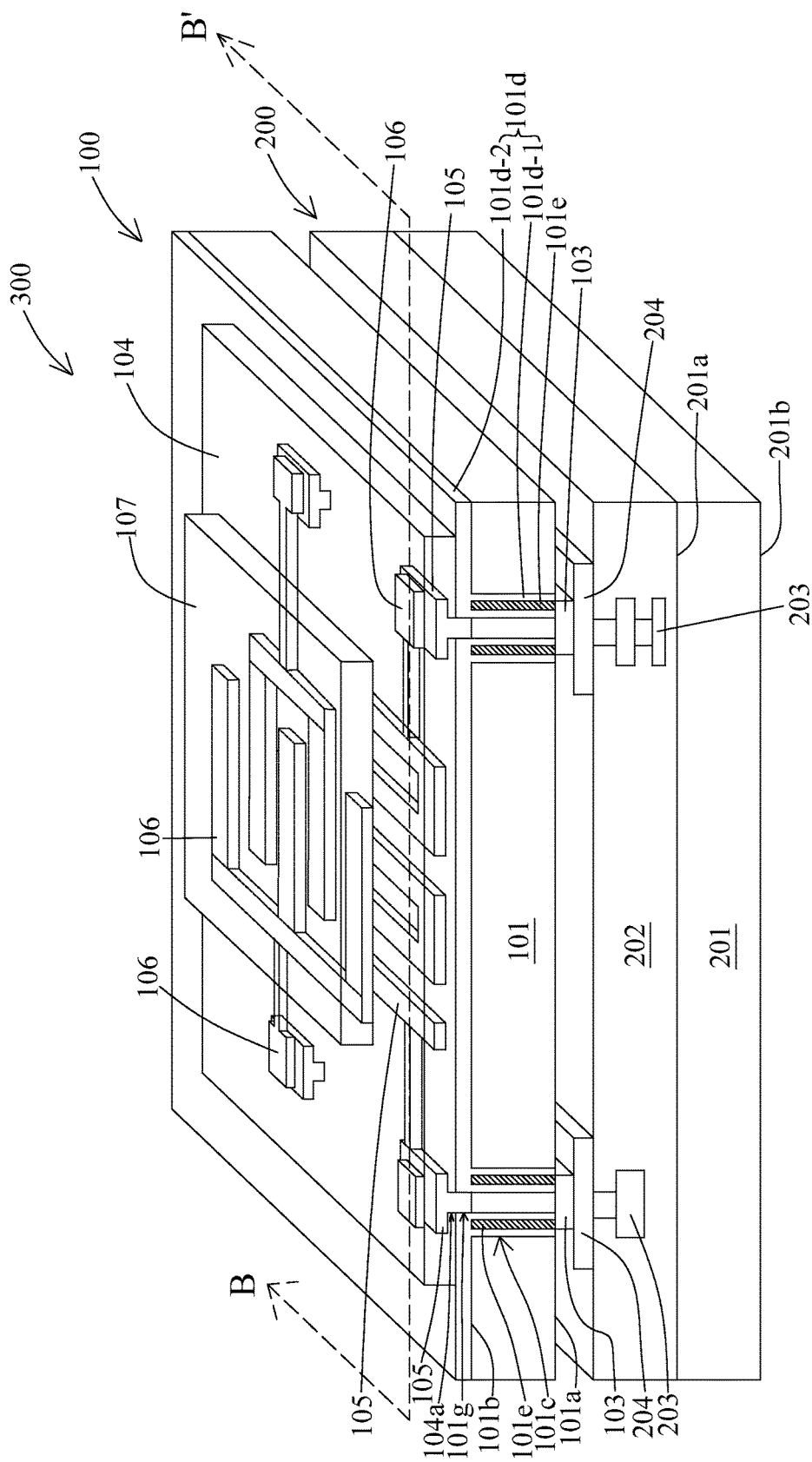
FIG. 4 is a schematic perspective view of a semiconductor structure in accordance with some embodiments of the present disclosure.
Figure 5:
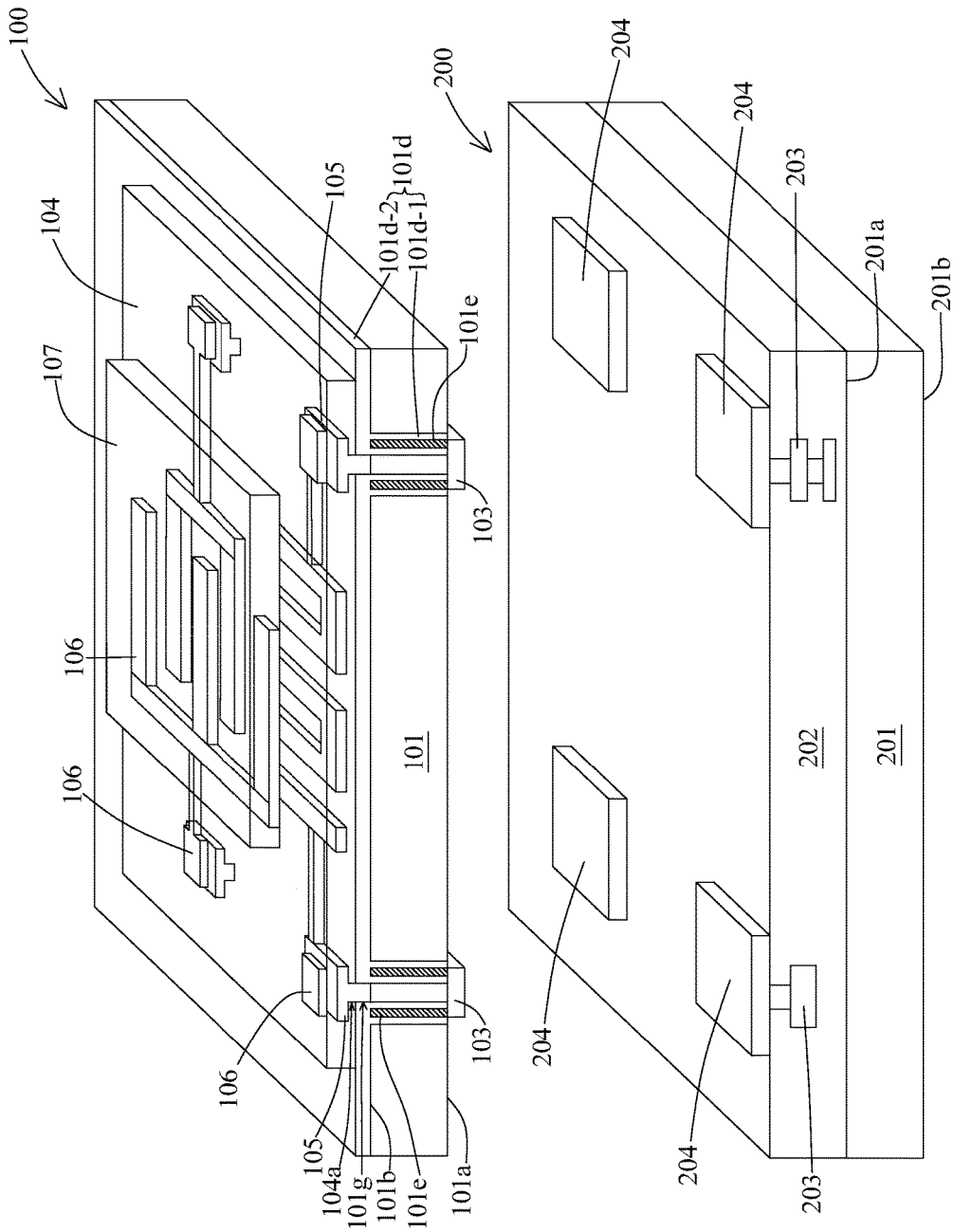
FIG. 5 is a schematic exploded view of a semiconductor structure of FIG. 4 in accordance with some embodiments of the present disclosure.
Figure 6:
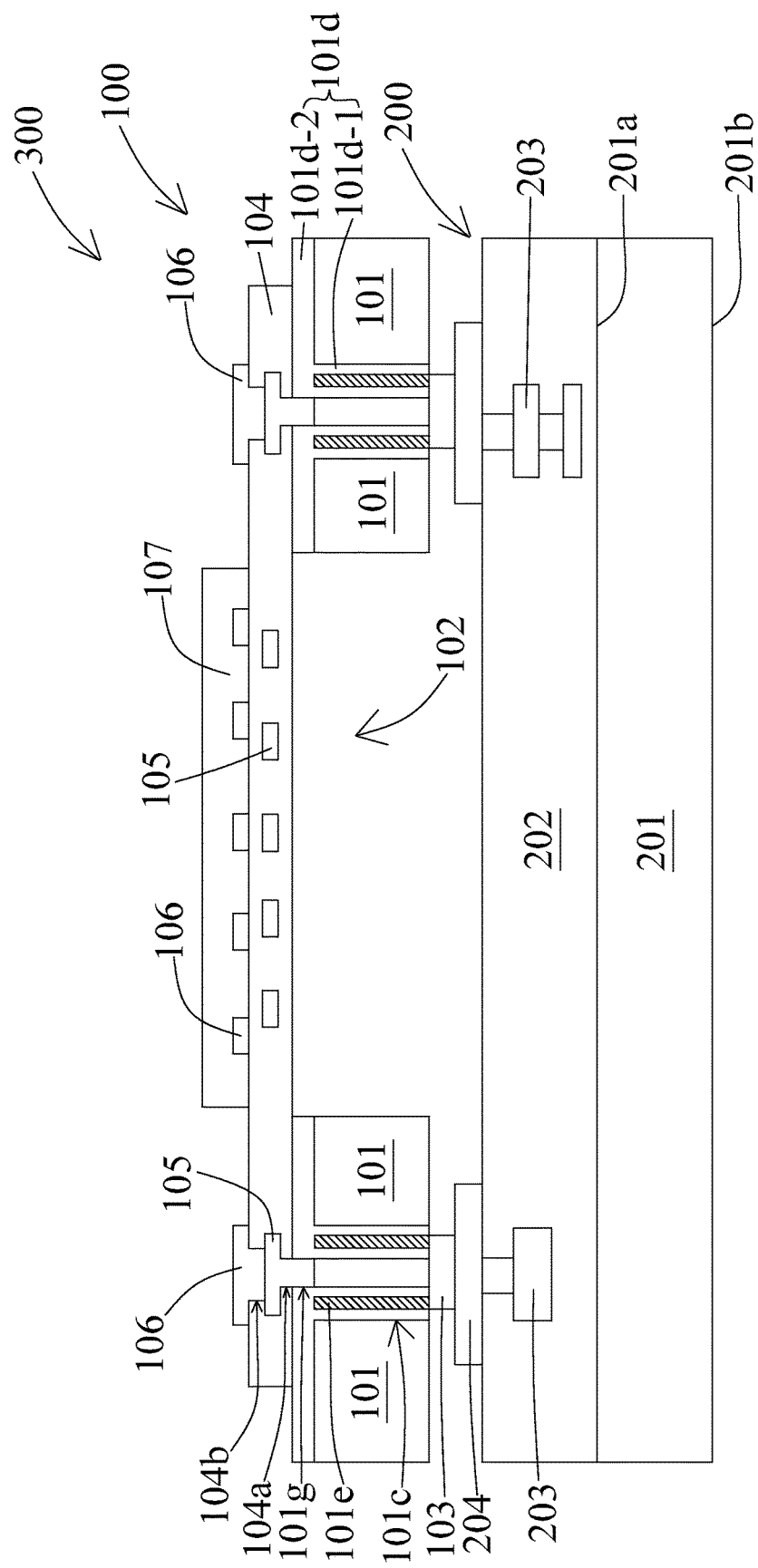
FIG. 6 is a schematic cross-sectional view of a semiconductor structure along BB' of FIG. 4 in accordance with some embodiments of the present disclosure.

FIG. 4 is a schematic perspective view of a semiconductor structure 300 in accordance with some embodiments of the present disclosure. The semiconductor structure 300 includes a first device 100 and a second device 200. FIG. 5 is a schematic exploded view of the semiconductor structure 300. FIG. 6 is a schematic cross sectional view of the semiconductor structure 300 along BB' of FIG. 4.

In some embodiments, the semiconductor structure 300 is configured for sensing a present of a predetermined material such as a gas. In some embodiments, the semiconductor structure 300 is a part of a sensor. In some embodiments, the semiconductor structure 300 is included in a gas sensor. In some embodiments, the semiconductor structure 300 is a monolithic sensor including the first device 100 integrated with the second device 200. In some embodiments, the semiconductor structure 300 includes the first device 100 which has similar configuration as the first device 100 described above or illustrated in any one of FIGS. 1-3.

In some embodiments, the semiconductor structure 300 includes the second device 200 disposed opposite to the first device 100. In some embodiments, the second device 200 is disposed under the first device 100. In some embodiments, the first device 100 is mounted on the second device 200. In some embodiments, the first device 100 is bonded with the second device 200, so that the first device 100 is integrated with the second device 200. In some embodiments, the second device 200 is a CMOS device including CMOS components.

In some embodiments, the second device 200 includes a second substrate 201 and a bonding structure 204 disposed over the second substrate 201. In some embodiments, the second substrate 201 includes CMOS components and circuitries disposed over or in the second substrate 201. In some embodiments, the second substrate 201 includes silicon or other suitable materials. In some embodiments, the second substrate 201 is a silicon substrate. In some embodiments, the second substrate 201 is a CMOS substrate. In some embodiments, the second substrate 201 includes a first surface 201a and a second surface 201b opposite to the first surface 201a. In some embodiments, the first surface 201a of the second substrate 201 is opposite to the first surface 101a of the first substrate 101. In some embodiments, the second substrate 201 has a thickness of about 500 um to about 750 um.

In some embodiments, an intermetallic dielectric (IMD) layer 202 is disposed over the second substrate 201. In some embodiments, the IMD layer 202 includes oxide such as silicon oxide or other suitable materials. In some embodiments, the IMD layer 202 is disposed over the first surface 201a of the second substrate 201. In some embodiments, an conductive structure 203 is disposed within the IMD layer 202. In some embodiments, the conductive structure 203 is electrically connected with the components or circuitries in the second substrate 201. In some embodiments, the conductive structure 203 includes tungsten, copper, aluminum, etc.

In some embodiments, the bonding structure 204 is disposed over the second substrate 201 and the IMD layer 202. In some embodiments, the bonding structure 204 is disposed over and electrically connected with the conductive structure 203. In some embodiments, the bonding structure 204 is configured to receive other conductive structure. In some embodiments, the bonding structure 204 includes germanium or other suitable materials. In some embodiments, the bonding structure 204 is extended over and across the IMD layer 202 or the first surface 201a of the second substrate 201. In embodiments, the bonding structure 204 is a bond pad.

In some embodiments, the bonding structure 204 is electrically connected and bonded with the metallic material 103 to integrate and electrically connect the first device 100 with the second device 200. In some embodiments, the sensing electrode 106 is electrically connected with the conductive structure 203 or the second substrate 201 by the bonding structure 204 and the metallic material 103. In some embodiments, when the predetermined material is present, an electrical signal generated by a change of a resistance of the sensing material 107 is transmitted from the first device 100 to the second device 200 for further processing.

Figure 7:
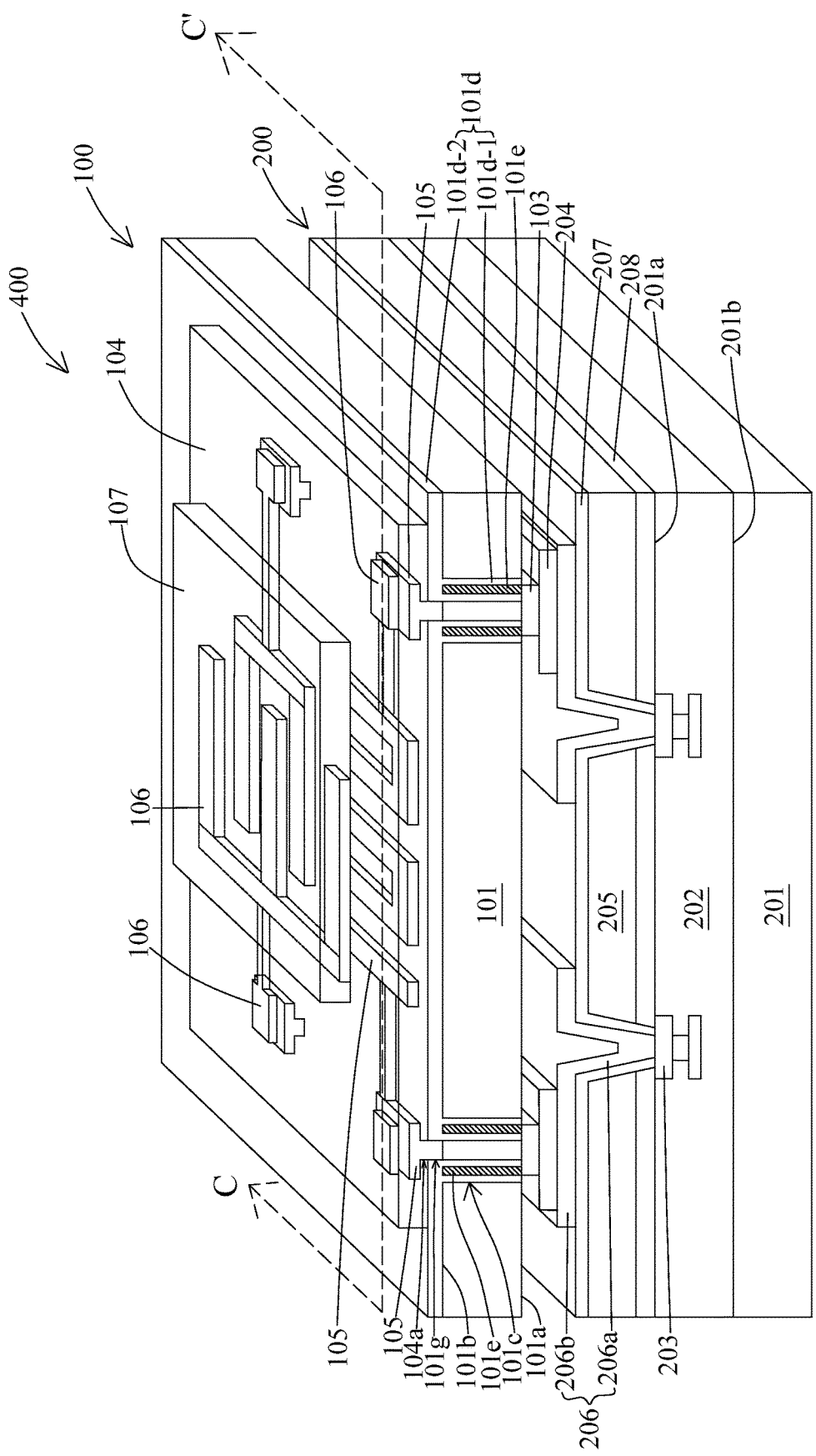
FIG. 7 is a schematic perspective view of a semiconductor structure in accordance with some embodiments of the present disclosure.
Figure 8:
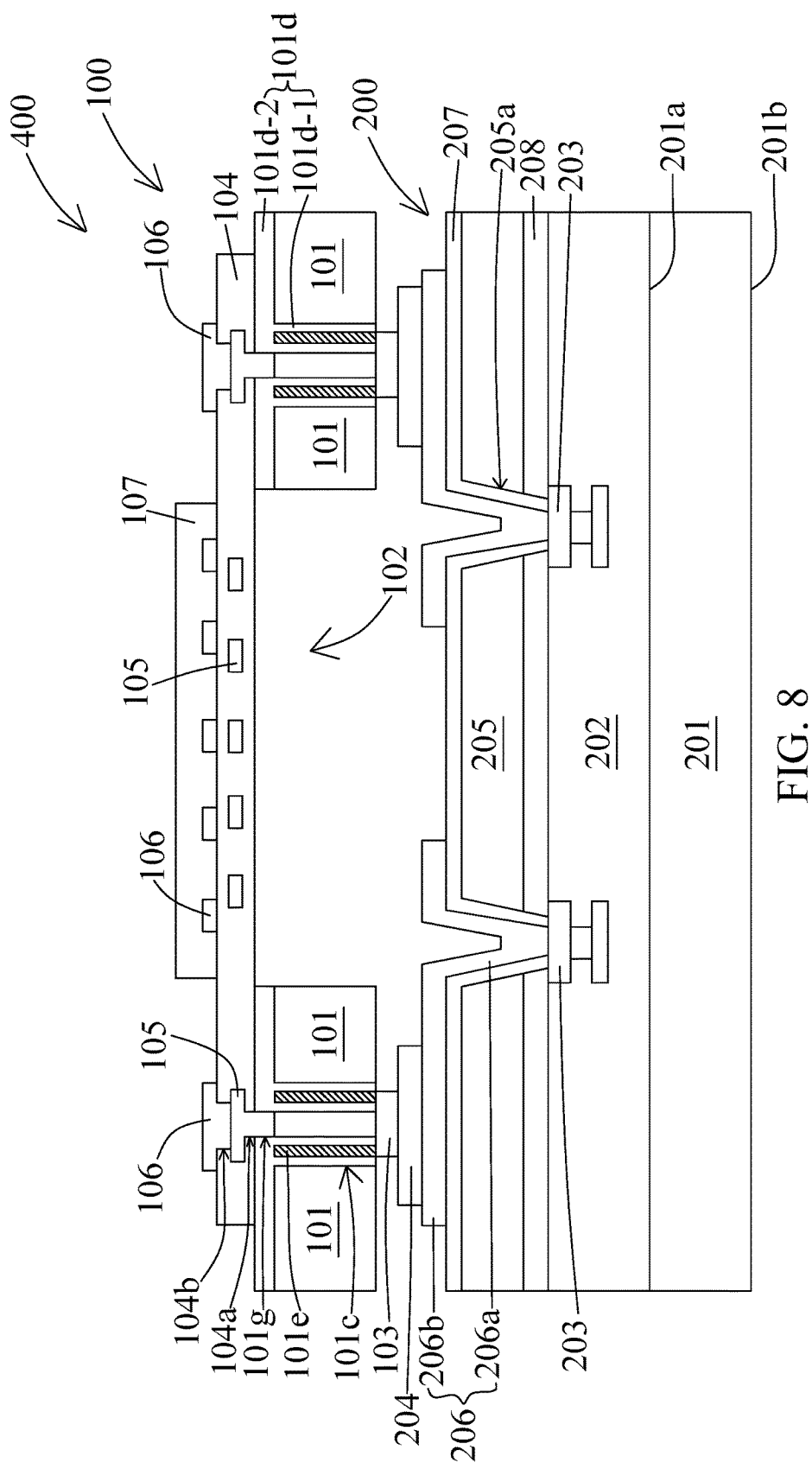
FIG. 8 is a schematic cross-sectional view of a semiconductor structure along CC' of FIG. 7 in accordance with some embodiments of the present disclosure.

FIG. 7 is a schematic perspective view of a semiconductor structure 400 in accordance with some embodiments of the present disclosure. The semiconductor structure 400 includes a first device 100 and a second device 200. FIG. 8 is a schematic cross sectional view of the semiconductor structure 400 along CC' of FIG. 7.

In some embodiments, the semiconductor structure 400 is configured for sensing a present of a predetermined material such as a gas. In some embodiments, the semiconductor structure 400 is a part of a sensor. In some embodiments, the semiconductor structure 400 is included in a gas sensor. In some embodiments, the semiconductor structure 400 is a monolithic sensor including the first device 100 integrated with the second device 200. In some embodiments, the semiconductor structure 400 includes the first device 100 which has similar configuration as the first device 100 described above or illustrated in any one of FIGS. 1-3. In some embodiments, the second device 200 includes a second substrate 201, an IMD layer 202, a conductive structure 203 and a bonding structure 204, which have similar configuration as described above or illustrated in any one of FIGS. 4-6.

In some embodiments, a dielectric layer 208 is disposed over the IMD layer 202. In some embodiments, the dielectric layer 208 includes oxide or other suitable dielectric materials. In some embodiments, the second device 200 includes an isolation layer 205 disposed over the CMOS substrate 201 and configured to thermally isolate the CMOS substrate 201 from the MEMS substrate 101. In some embodiments, the present of the isolation layer 205 increases a distance between the CMOS substrate 201 and the MEMS substrate 101 or a distance between the first device 100 and the second device 200, such that a heat provided by the heater 105 would not affect the CMOS substrate 201 or the second device 200. In some embodiments, the isolation layer 205 includes silicon or other suitable materials. In some embodiments, the isolation layer 205 is a silicon substrate or silicon wafer. In some embodiments, the isolation layer 205 includes dielectric material such as silicon oxide, silicon nitride, etc. In some embodiments, the isolation layer 205 is a passivation. In some embodiments, the isolation layer 205 has a thickness of about 30 um to about 300 um.

In some embodiments, the isolation layer 205 includes several fourth recesses 205a disposed over the conductive structure 203. In some embodiments, the fourth recesses passes through the isolation layer 205 and the dielectric layer 208 to expose a portion of the conductive structure 203, such that the conductive structure 203 can electrically connect with external circuitry or components.

In some embodiments, a third oxide layer 207 is disposed over the isolation layer 205. In some embodiments, the third oxide layer 207 is disposed conformal to the fourth recesses 205. In some embodiments, the third oxide layer 207 includes silicon oxide or other suitable materials. In some embodiments, the third oxide layer 207 has a thickness of about 0.1 um to about 5 um.

In some embodiments, an interconnect structure 206 is disposed over the isolation layer 205, the third oxide layer 207 and the conductive structure 203. In some embodiments, the interconnect structure 206 includes conductive material such as aluminum, copper, etc. In some embodiments, the interconnect structure 206 is a redistribution layer (RDL).

In some embodiments, the interconnect structure 206 includes a via portion 206a and an elongated portion 206b. In some embodiments, the via portion 206a passes through the isolation layer 205 and contacts with the conductive structure 203 or the IMD layer 202. In some embodiments, the via portion 206a is extended from the isolation layer 205 to the IMD layer 202 and is disposed over the conductive structure 203. In some embodiments, the via portion 206a is electrically connected with the conductive structure 203. In some embodiments, the via portion 206a is conformal to the third oxide layer 207 disposed within the fourth recess 205a. In some embodiments, the third oxide layer 207 is disposed between the via portion 206a and the isolation layer 205.

In some embodiments, the interconnect structure 206 includes an elongated portion 206b extending over and along the isolation layer 205. In some embodiments, the elongated portion 206b is disposed over the third oxide layer 207. In some embodiments, the elongated portion 206b is electrically connected with the conductive structure 203 through the via portion 206a.

In some embodiments, the elongated portion 206b is configured to receive the bonding structure 204. The bonding structure 204 is disposed over the elongated portion 206b, so that the interconnect structure 206 is electrically connected with the bonding structure 204. In some embodiments, the CMOS substrate 201 and the MEMS substrate 101 are integrated by bonding the metallic material 103 with the bonding structure 204 and electrically connecting the CMOS substrate 201 with the MEMS substrate 101. In some embodiments, the elongated portion 206b is bonded with the bonding structure 204, and the bonding structure 204 is bonded with the metallic material 103. Thus, the first device 100 is bonded and integrated with the second device 200 by the metallic structure 103, the bonding structure 204 and the elongated portion 206b.

In the present disclosure, a method of manufacturing a semiconductor structure is also disclosed. In some embodiments, a semiconductor structure is formed by a method 500. The method 500 includes a number of operations and the description and illustration are not deemed as a limitation as the sequence of the operations.

Figure 9:
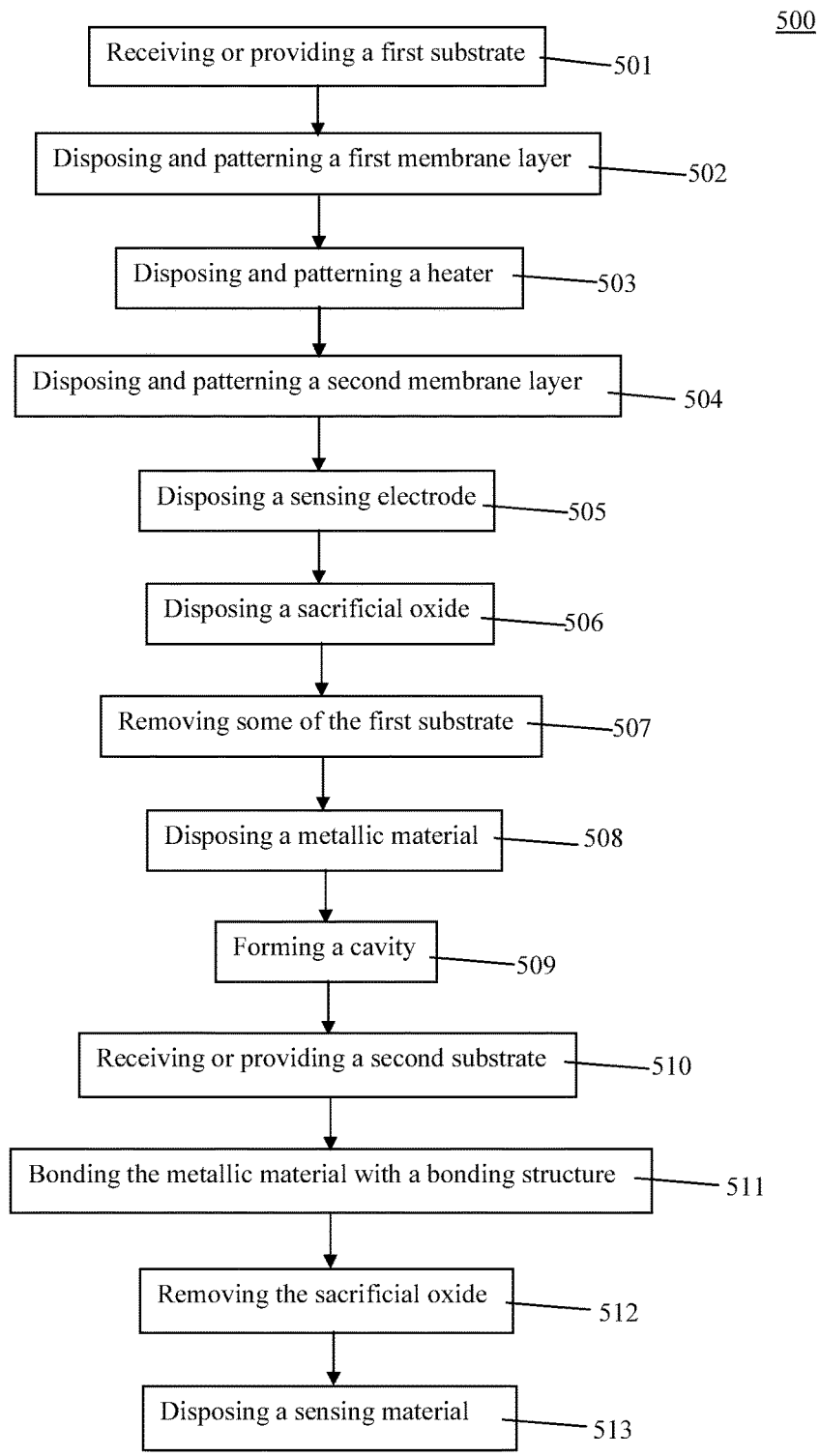
FIG. 9 is a flow diagram of a method of manufacturing a semiconductor structure in accordance with some embodiments of the present disclosure.

FIG. 9 is an embodiment of a method 500 of manufacturing a semiconductor structure. The method 500 includes a number of operations (501, 502, 503, 504, 505, 506, 507, 508, 509, 510, 511, 512 and 513).

In Operation 501, a first substrate 101 is received or provided as shown in FIG. 9A. In some embodiments, the first substrate 101 includes silicon, glass, ceramic or other suitable materials. In some embodiments, the first substrate 101 is a silicon substrate. In some embodiments, the first substrate 101 includes electrical circuits formed on or in the first substrate 101. In some embodiments, the first substrate 101 includes a first surface 101a and a second surface 101b opposite to the first surface 101a. In some embodiments, the first surface 101a is a back side of the first substrate 101, while the second surface 101b is a front side of the first substrate 101.

In some embodiments, the first substrate 101 includes several vias 101c extending from the second surface 101b towards the first surface 101a. In some embodiments, the vias 101c are formed by photolithography and etching operations. In some embodiments, a first oxide layer 101d-1 is disposed conformal to the vias 101c. In some embodiments, the first oxide layer 101d-1 is formed within the vias 101c by thermal oxidation operations.

In some embodiments, each via 101c is filled by a conductive or semiconductive material 101e. In some embodiments, the conductive or semiconductive material 101e includes polysilicon. The first oxide layer 101d-1 is disposed between the first substrate 101 and the conductive or semiconductive material 101e. In some embodiments, the conductive or semiconductive material 101e is formed by deposition operations such as chemical vapor deposition (CVD), low pressure CVD (LPCVD), etc. In some embodiments, the conductive or semiconductive material 101e is polished or planarized by suitable operations such as chemical mechanical planarization (CMP).

In some embodiments, a second oxide layer 101d-2 is disposed over the first surface 101a or the second surface 101b of the first substrate 101. In some embodiments, the second oxide layer 101d-2 is disposed over the vias 101c and contacts with the first oxide layer 101d-1 and the conductive or semiconductive material 101e. In some embodiments, the second oxide layer 101d-2 is formed by thermal oxidation operations. In some embodiments, the second oxide layer 101d-2 is same material as or different material from the first oxide layer 101d-1.

In operation 502, a first membrane layer 104-1 is disposed and patterned over the second oxide layer 101d-2 as shown in FIG. 9B. In some embodiments, the first membrane layer 104-1 is disposed over the second oxide layer 101d-2, and then patterned to form several second recesses 104a. In some embodiments, the first membrane layer 104-1 is also disposed over the first surface 101a of the first substrate 101. In some embodiments, the first membrane layer 104-1 includes silicon, silicon dioxide, silicon nitride, silicon carbide, porous silicon, composite film or other suitable materials. In some embodiments, the first membrane layer 104-1 is disposed by CVD or other suitable operations.

In some embodiments, the second recesses 104a are formed by removing some of the first membrane layer 104-1 disposed between the vias 101c. In some embodiments, the first membrane layer 104-1 is patterned to form the second recesses 104a by photolithography and etching operations. In some embodiments, some of the second oxide layer 101d-2 disposed under the second recesses 104a are also removed to form several first recesses 101g, and thus the first recesses 101g are coupled with the second recesses 104a respectively. In some embodiments, the first recess 101g passes through the second oxide layer 101d-2 and extends to the second surface 101b of the first substrate 101.

Figure 9C:
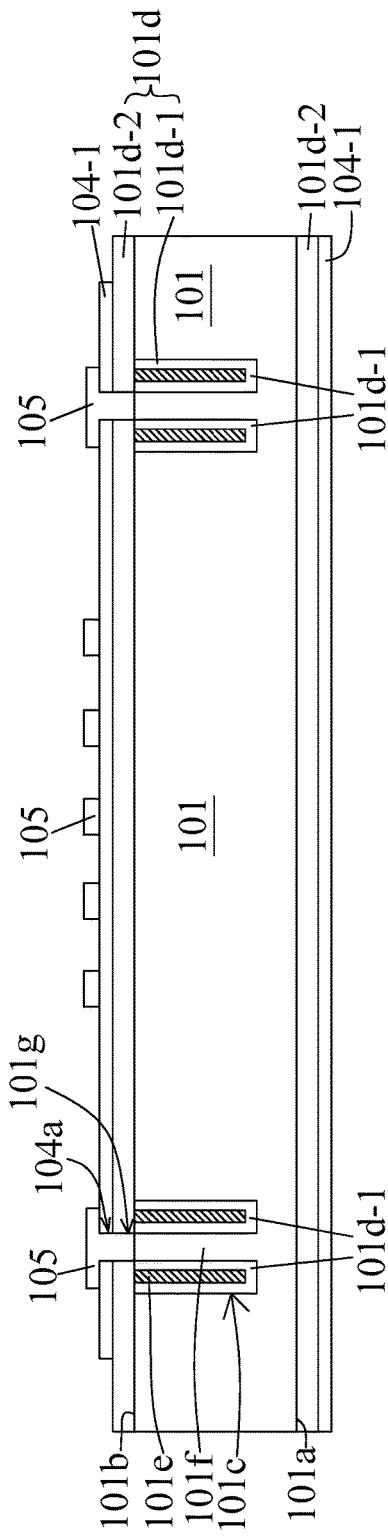
FIG. 9C is a cross-sectional view of a first substrate with a heater in accordance with some embodiments of the present disclosure.

In operation 503, a heater 105 is disposed and patterned over the first membrane layer 104-1 as shown in FIG. 9C. In some embodiments, the heater 105 is disposed over the second oxide layer 101d-2, and then patterned by photolithography and etching operations. In some embodiments, the heater 105 is disposed over the second oxide layer 101d-2 and within the first recesses 101g and the second recesses 104a. In some embodiments, the heater 105 is electrically connected with a portion 101f of the first substrate 101 disposed between the vias 101c. In some embodiments, the heater 105 includes tungsten alloy, tungsten silicide (WSi) titanium tungsten (TiW), titanium aluminum nitride (TiAlN), tantalum aluminum (TaAl), chromium (Cr), platinum (Pt), titanium nitride (TiN), molybdenum (Mo), polysilicon, silicon carbide (SiC), tantalum nitride (TaN), tantalum oxide (TaO) or other suitable materials.

Figure 9D:
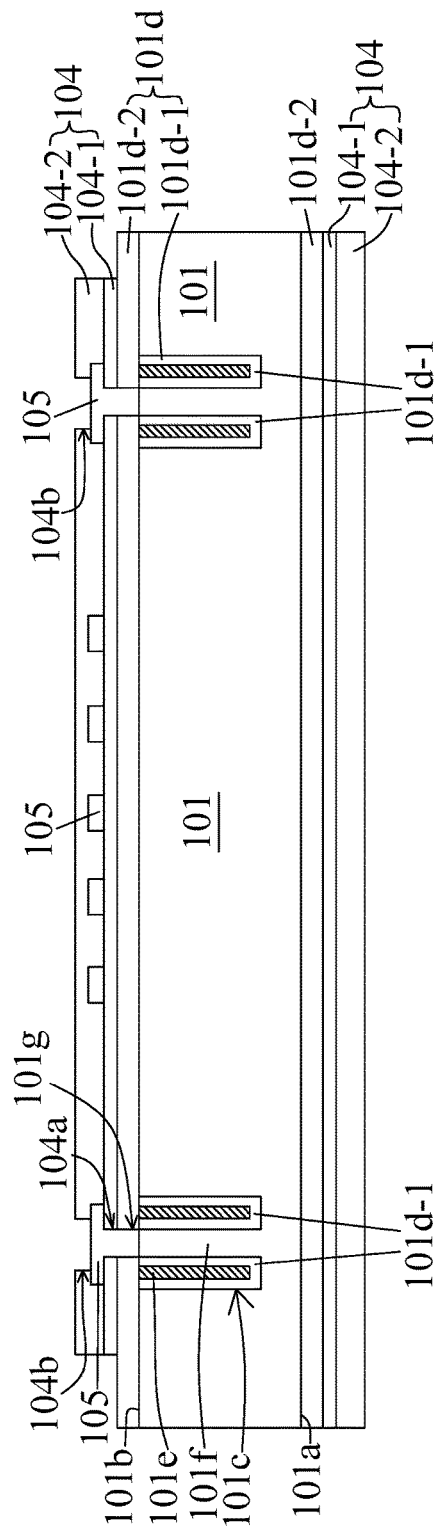
FIG. 9D is a cross-sectional view of a first substrate with a second membrane layer in accordance with some embodiments of the present disclosure.

In operation 504, a second membrane layer 104-2 is disposed and patterned over the heater 105 and the first membrane layer 104-1 as shown in FIG. 9D. In some embodiments, the second membrane layer 104-2 is disposed over the first membrane layer 104-1, and then patterned to form several third recesses 104b. In some embodiments, the second membrane layer 104-2 is also disposed over the first surface 101a of the first substrate 101. In some embodiments, the second membrane layer 104-2 includes silicon, silicon dioxide, silicon nitride, silicon carbide, porous silicon, composite film or other suitable materials. In some embodiments, the second membrane layer 104-2 includes same material as or different material from the first membrane layer 104-1. In some embodiments, the second membrane layer 104-2 is disposed by CVD or other suitable operations. In some embodiments, the first membrane layer 104-1 and the second membrane layer 104-2 become a membrane 104. The heater 105 is disposed within the membrane 104.

In some embodiments, the third recesses 104b are formed by removing some of the second membrane layer 104-2 disposed over the second recesses 104a. In some embodiments, the second membrane layer 104-2 is patterned to form the third recesses 104b by photolithography and etching operations. In some embodiments, the third recess 104b extends towards the heater 105 disposed within the second recess 104a.

In operation 505, a sensing electrode 106 is disposed over the second membrane layer 104-2 as shown in FIG. 9E. In some embodiments, the sensing electrode 106 is disposed over the second membrane layer 104-2 and within the third recesses 104b. In some embodiments, the sensing electrode 106 is disposed over the heater 105. In some embodiments, a portion of the sensing electrode 106 is coupled with a portion of the heater 105 through the third recess 104b. In some embodiments, the sensing electrode 106 is patterned by photolithography and etching operations. In some embodiments, the sensing electrode 106 is configured to sense a predetermined material such as a gas. In some embodiments, the sensing electrode 106 includes tungsten alloy, titanium tungsten (TiW), titanium aluminum nitride (TiAlN), tantalum aluminum (TaAl), titanium, titanium nitride (TiN), tantalum, tantalum nitride (TaN), tantalum oxide (TaO), tantalum silicon nitride (TaSiN), platinum (Pt), or other suitable materials.

In operation 506, a sacrificial oxide 108 is disposed over the sensing electrode 106 and the second membrane layer 104-2 as shown in FIG. 9F. In some embodiments, the sacrificial oxide 108 covers the sensing electrode 106 and the second membrane layer 104-2 for protection. In some embodiments, the sacrificial oxide 108 is deposited by suitable operations such as CVD. In some embodiments, the sacrificial oxide 108 is polished and planarized by suitable operations such as chemical mechanical planarization (CMP).

Figure 9G:
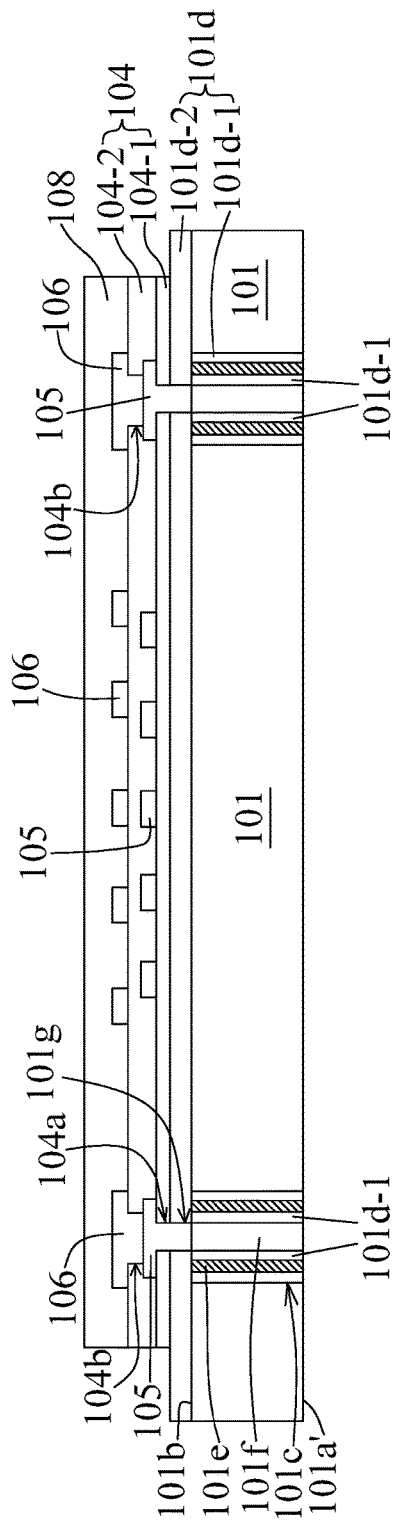
FIG. 9G is a cross-sectional view of a first substrate with a reduced thickness in accordance with some embodiments of the present disclosure.

In operation 507, some of the first substrate 101 are removed from the first surface 101a to expose the conductive or semiconductive material 101e as shown in FIG. 9G. In some embodiments, some of the first substrate 101, the second oxide layer 101d-2, the first membrane layer 104-1 and the second membrane layer 104-2 disposed over the first surface 101a are removed by suitable operations such as grinding, etching, etc. In some embodiments, the removal of some of the first surface 101a is backside grinding operations. In some embodiments, some of the first substrate 101 are removed by grinding the first surface 101a towards the second surface 101b. In some embodiments, a thickness of the first substrate 101 is reduced by grinding over the first surface 101a, such that a new first surface 101a' is formed and the conductive or semiconductive material 101e is exposed.

Figure 9H:
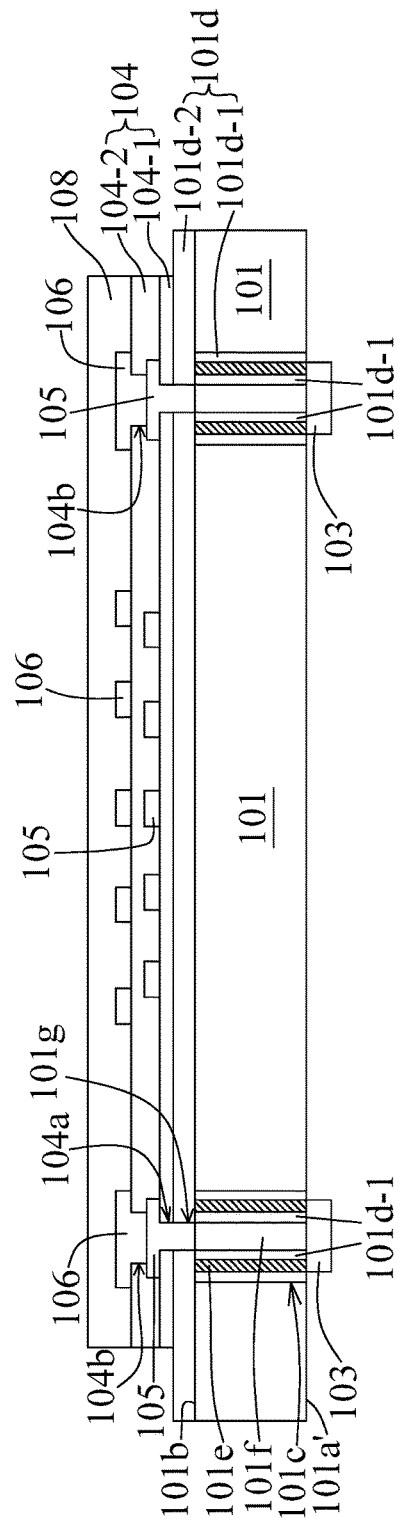
FIG. 9H is a cross-sectional view of a first substrate with a metallic material in accordance with some embodiments of the present disclosure.

In operation 508, a metallic material 103 is disposed over the new first surface 101a' and the vias 101c as shown in FIG. 9H. In some embodiments, the metallic material 103 is disposed and then patterned by photolithography and etching operations, such that the metallic material 103 is formed over the portion 101f of the first substrate 101 and the vias 101c. In some embodiments, the metallic material 103 is disposed by electroplating, sputtering or other suitable operations. In some embodiments, the first substrate 101 is flipped before formation of the metallic material 103. In some embodiments, the metallic material 103 is configured to electrically connect with a circuitry external to the first substrate 101. In some embodiments, the metallic material 103 is configured to receive a bonding structure. In some embodiments, the metallic material 103 includes copper, aluminum, aluminum copper alloy or other suitable materials.

Figure 9I:
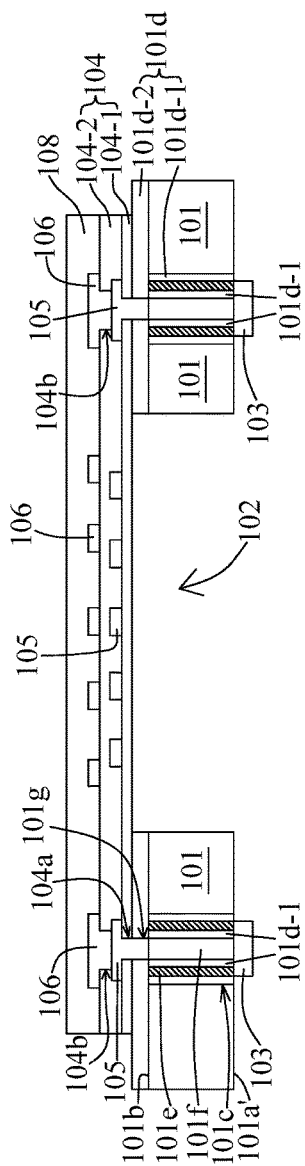
FIG. 9I is a cross-sectional view of a first substrate with a cavity in accordance with some embodiments of the present disclosure.

In operation 509, a cavity 102 is formed as shown in FIG. 9I. In some embodiments, some of the first substrate 101 are removed to form the cavity 102 by photolithography and etching operations. In some embodiments, some of the first substrate 101 are etched from the new first surface 101a' through the second surface 101b to expose the first membrane layer 104-1 or the second oxide layer 101d-2. In some embodiments, some of the first substrate 101 are etched until reaching the second oxide layer 101d-2. In some embodiments, some of the first substrate 101 and some of the second oxide layer 101d-2 are removed to form the cavity 102.

Figure 9J:
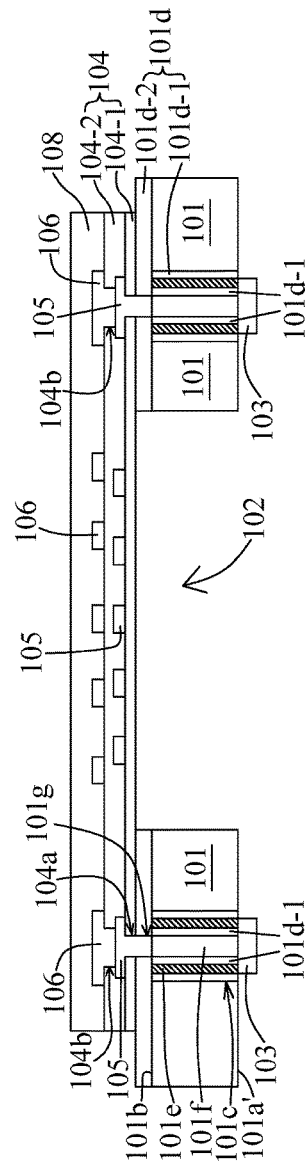
FIG. 9J is a cross-sectional view of a first substrate and a second substrate in accordance with some embodiments of the present disclosure.
Figure 9J:
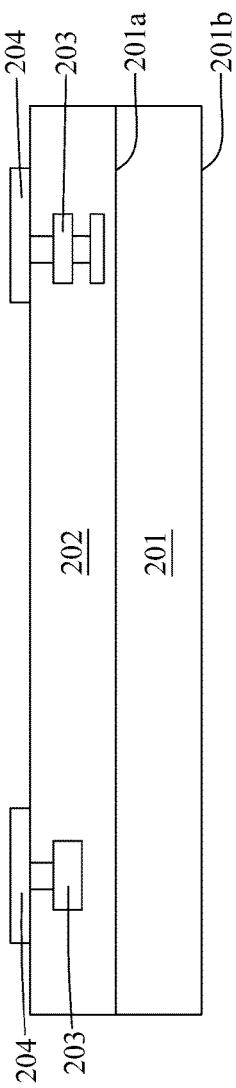

In operation 510, a second substrate 201 is received or provided as shown in FIG. 9J. In some embodiments, the second substrate 201 includes a first surface 201a and a second surface 201b opposite to the first surface 201a. In some embodiments, the second substrate 201 includes CMOS components and circuitries disposed over or in the second substrate 201. In some embodiments, the second substrate 201 includes silicon or other suitable materials. In some embodiments, the second substrate 201 is a silicon substrate. In some embodiments, the second substrate 201 includes a bonding structure 204 disposed over the second substrate 201. In some embodiments, the bonding structure 204 is configured to receive the metallic material 103. In some embodiments, an IMD layer 202 is disposed over the second substrate 201, and a conductive structure 203 is disposed within the DAD layer 202. In some embodiments, the conductive structure 203 is disposed under and is electrically connected with the bonding structure 204.

In operation 511, the bonding structure 204 and the metallic material 103 are bonded as shown in FIG. 9K. In some embodiments, the first substrate 101 is disposed over the second substrate 201, and then the metallic material 103 is disposed and bonded with the bonding structure 204. In some embodiments, the metallic material 103 is bonded with the bonding structure 204 by eutectic bonding operations. In some embodiments, the bonding structure 204 includes germanium, and the metallic material 103 includes aluminum.

In operation 512, the sacrificial oxide 108 is removed as shown in FIG. 9L. In some embodiments, the sacrificial oxide 108 is removed to expose the sensing electrode 106 by etching operations such as wet etching or other suitable operations.

Figure 9M:
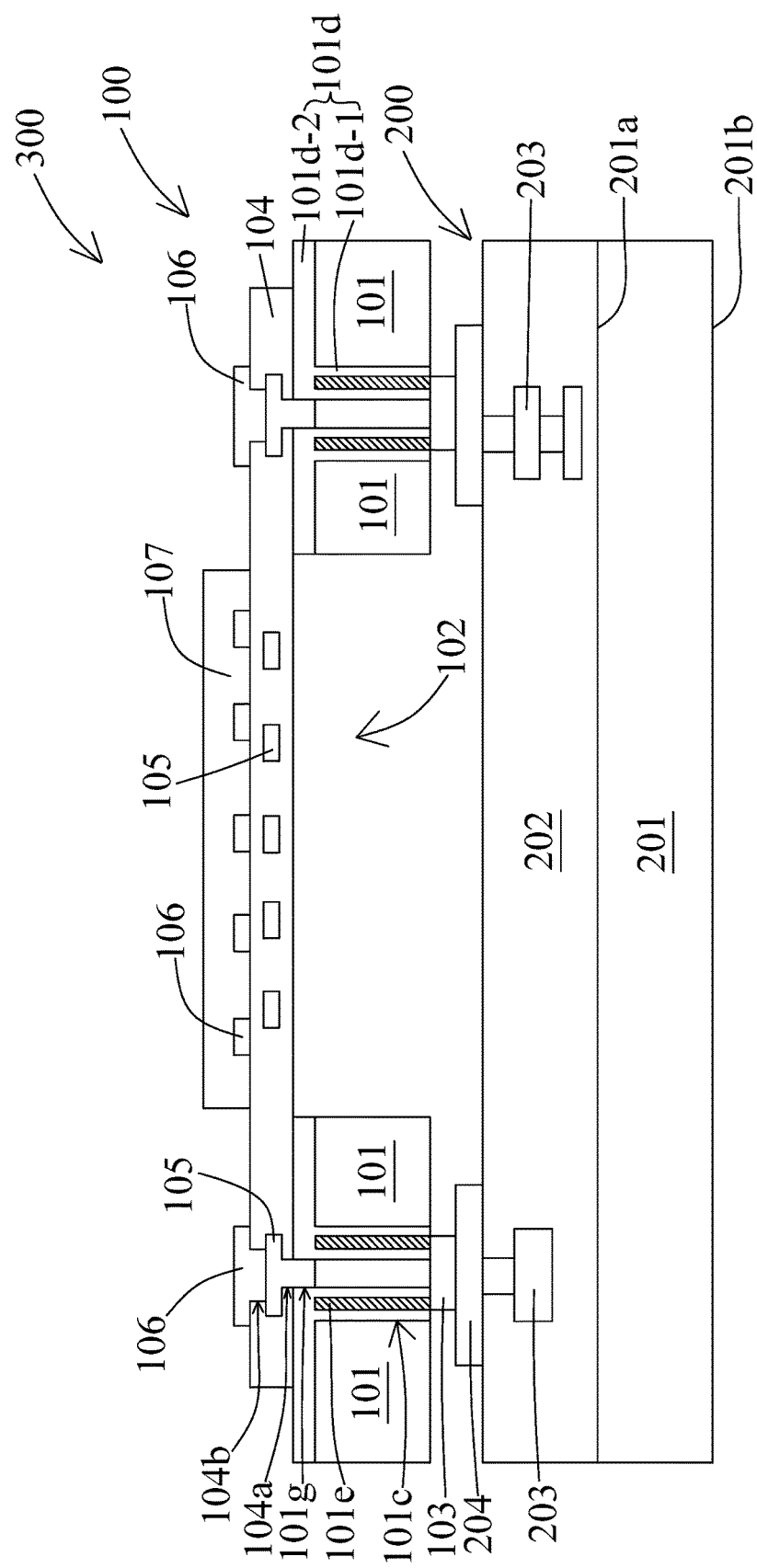
FIG. 9M is a cross-sectional view of a semiconductor structure in accordance with some embodiments of the present disclosure.

In operation 513, a sensing material 107 is disposed over the sensing electrode 106 as shown in FIG. 9M. In some embodiments, the sensing material 107 is disposed over the cavity 102 and contacts with the sensing electrode 106. In some embodiments, the sensing material 107 partially covers the sensing electrode 106, such that a portion of the sensing electrode 106 is encapsulated by the sensing material 107 while another portion of the sensing electrode 106 is extended out from the sensing material 107 and is not covered by the sensing material 107. In some embodiments, the sensing material includes tin dioxide ($SnO_2$), zinc oxide (ZnO), indium oxide ($In_2O_3$) or other suitable materials.

In some embodiments, a semiconductor structure 300 including a first device 100 and second device 200 is formed. The semiconductor structure 300, the first device 100 and the second device 200 have similar configuration as in any one of FIGS. 1-6. In some embodiments, the sensing material 107 is configured to detect a predetermined material under the operating temperature. In some embodiment, a resistance of the sensing material 107 would change when the predetermined material is present and contacted with the sensing material 107. The resistance of the sensing material 107 is varied by a chemical reaction between the sensing material 107 and the predetermined material. The change of the resistance of the sensing material 107 is sensed by the sensing electrode 106.

Figure 10:
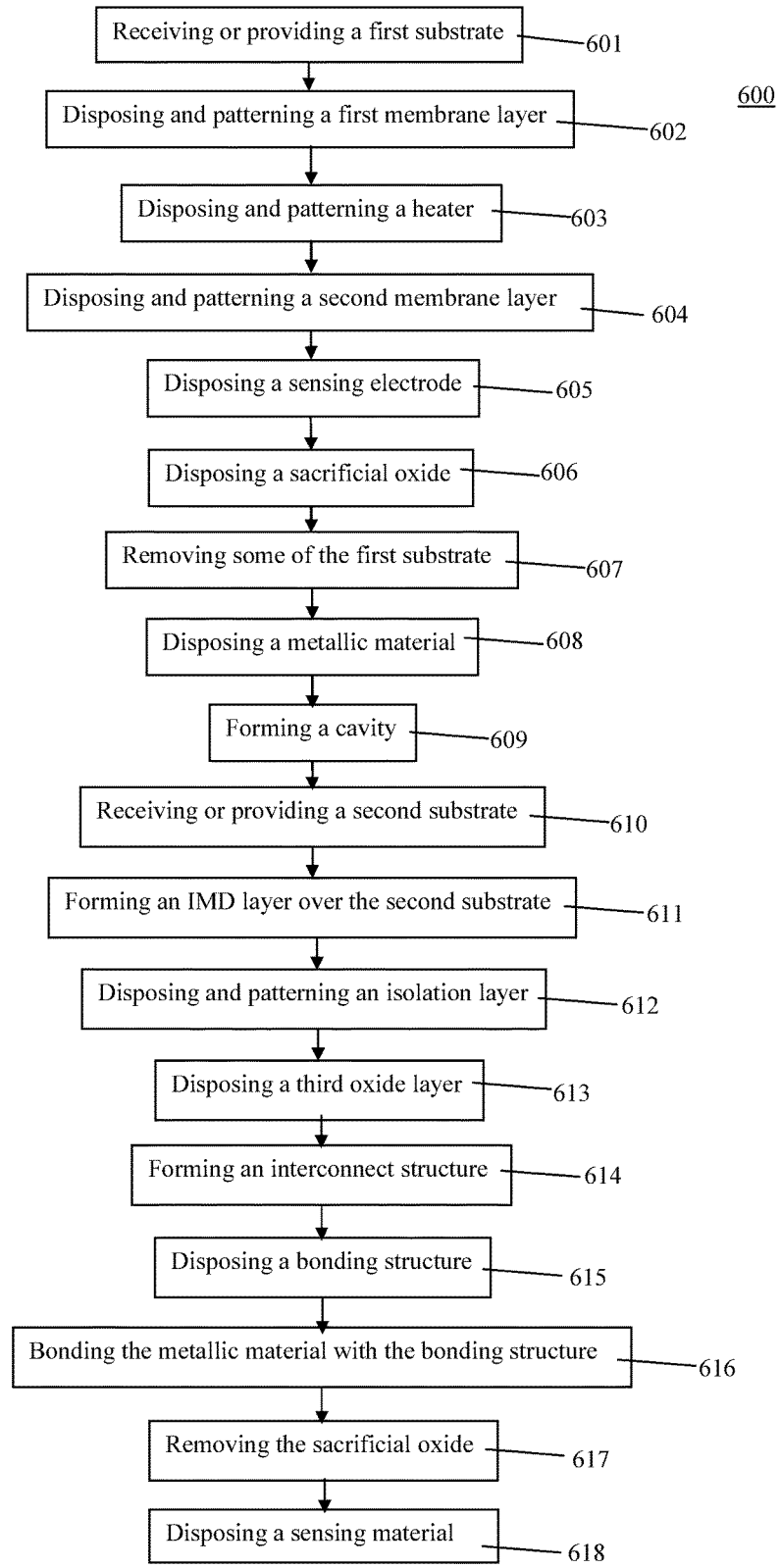
FIG. 10 is a flow diagram of a method of manufacturing a semiconductor structure in accordance with some embodiments of the present disclosure.

FIG. 10 is an embodiment of a method 600 of manufacturing a monolithic sensor. The method 600 includes a number of operations (601, 602, 603, 604, 605, 606, 607, 608, 609, 610, 611, 612, 613, 614, 615, 616, 617 and 618).

Figure 10C:
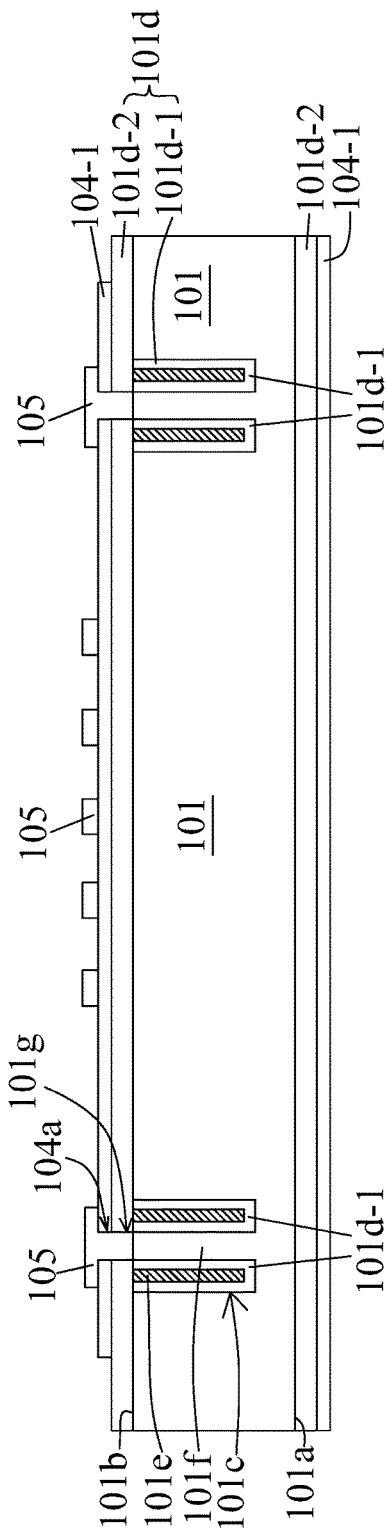
FIG. 10C is a cross-sectional view of a first substrate with a heater in accordance with some embodiments of the present disclosure.
Figure 10D:
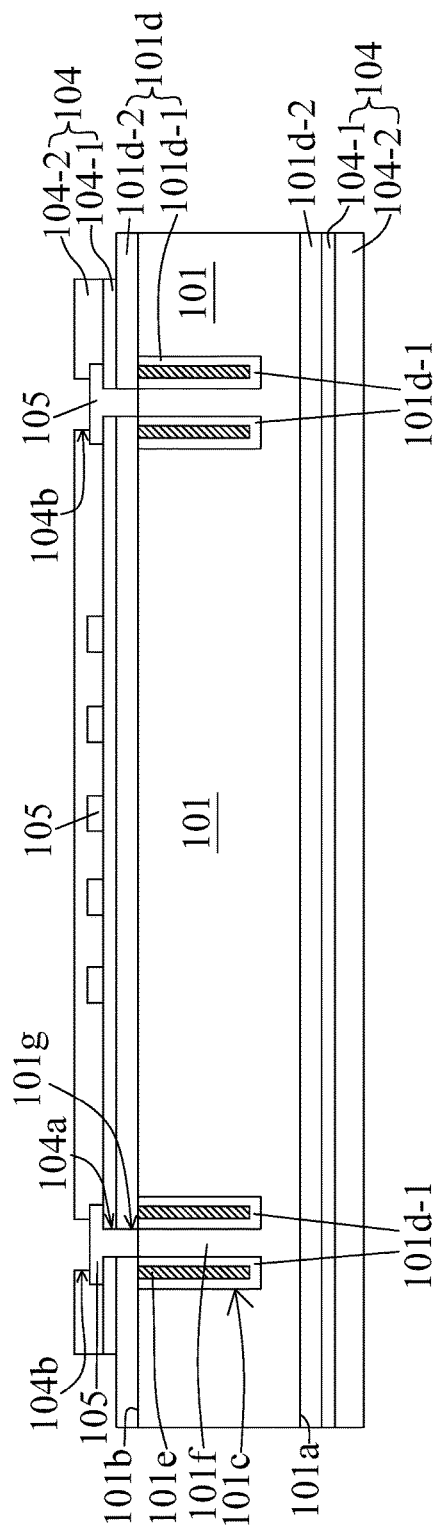
FIG. 10D is a cross-sectional view of a first substrate with a second membrane layer in accordance with some embodiments of the present disclosure.
Figure 10G:
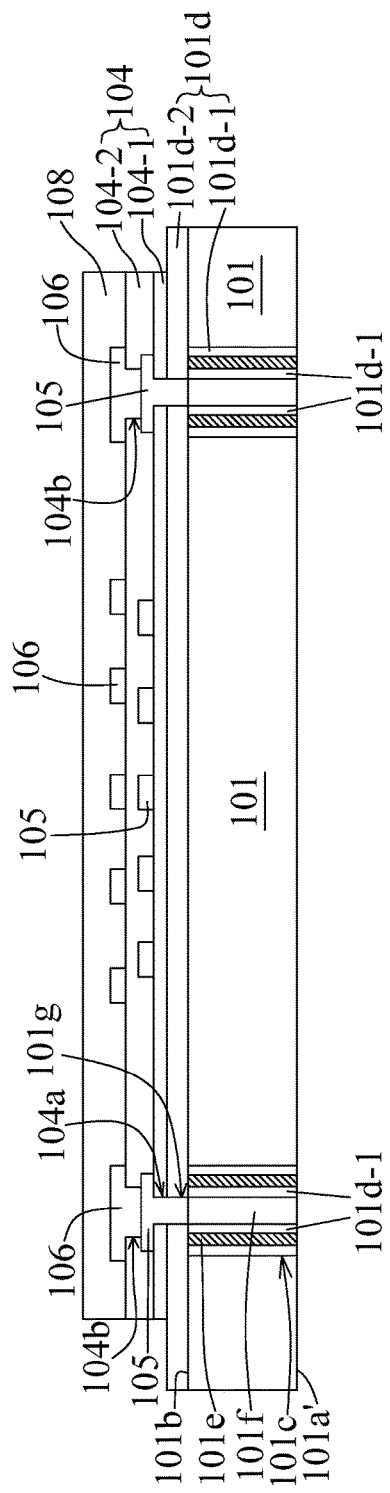
FIG. 10G is a cross-sectional view of a first substrate with a reduced thickness in accordance with some embodiments of the present disclosure.
Figure 10H:
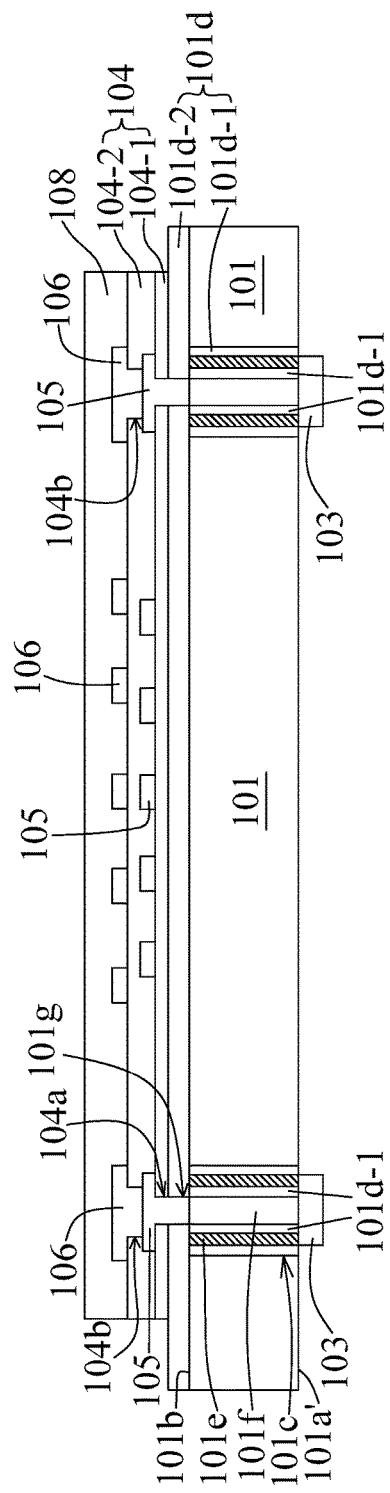
FIG. 10H is a cross-sectional view of a first substrate with a metallic material in accordance with some embodiments of the present disclosure.
Figure 10I:
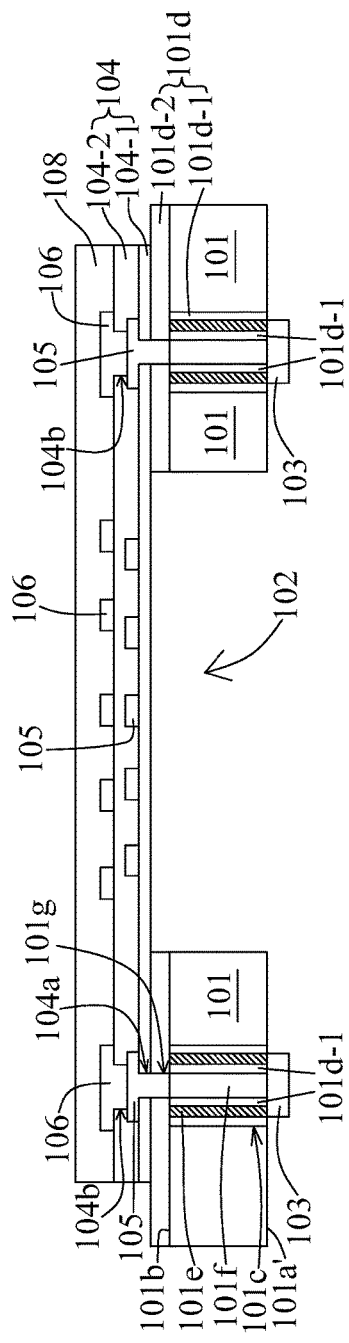
FIG. 10I is a cross-sectional view of a first substrate with a cavity in accordance with some embodiments of the present disclosure.

In operation 601, a first substrate 101 is received or provided as shown in FIG. 10A. The operation 601 is similar to the operation 501 in FIG. 9A. In operation 602, a first membrane layer 104-1 is disposed and patterned as shown in FIG. 10B. The operation 602 is similar to the operation 502 in FIG. 9B. In operation 603, a heater 105 is disposed and patterned as shown in FIG. 10C. The operation 603 is similar to the operation 503 in FIG. 9C. In operation 604, a second membrane layer 104-2 is disposed and patterned as shown in FIG. 10D. The operation 604 is similar to the operation 504 in FIG. 9D. In operation 605, a sensing electrode 106 is disposed as shown in FIG. 10E. The operation 605 is similar to the operation 505 in FIG. 9E. In operation 606, a sacrificial oxide 108 is disposed and patterned as shown in FIG. 10F. The operation 606 is similar to the operation 506 in FIG. 9F. In operation 607, some of the first substrate 101 are removed as Shown in FIG. 10G. The operation 607 is similar to the operation 507 in FIG. 9G. In operation 608, a metallic material 103 is disposed as shown in FIG. 10H. The operation 608 is similar to the operation 508 in FIG. 9H. In operation 609, a cavity 102 is formed as shown in FIG. 10I. The operation 609 is similar to the operation 509 in FIG. 9I.

Figure 10J:
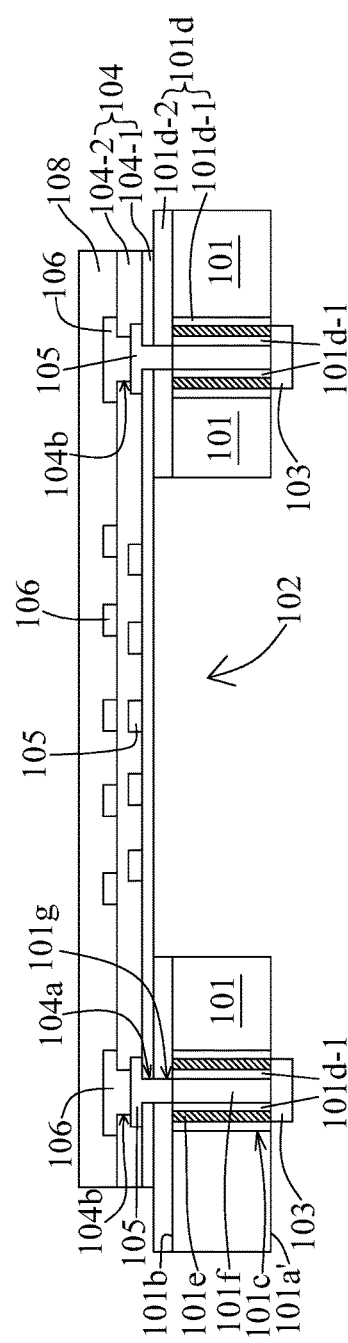
FIG. 10J is a cross-sectional view of a first substrate and a second substrate in accordance with some embodiments of the present disclosure.

In operation 610, a second substrate 201 is received or provided as shown in FIG. 10J. In some embodiments, the second substrate 201 includes a first surface 201a and a second surface 201b opposite to the first surface 201a. In some embodiments, the second substrate 201 includes CMOS components and circuitries disposed over or in the second substrate 201. In some embodiments, the second substrate 201 includes silicon or other suitable materials. In some embodiments, the second substrate 201 is a silicon substrate.

Figure 10K:
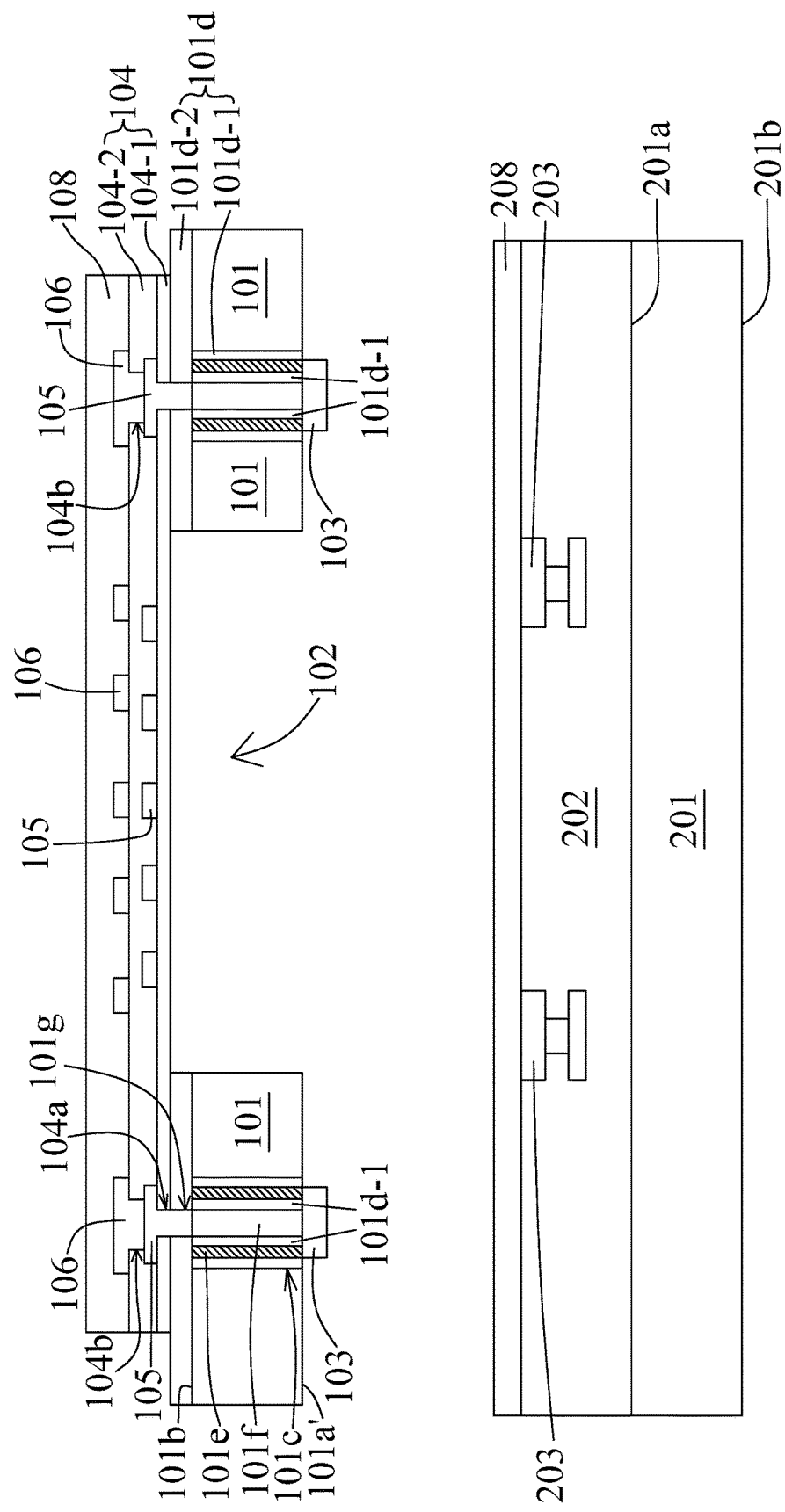
FIG. 10K is a cross-sectional view of a second substrate with an IMD layer in accordance with some embodiments of the present disclosure.

In operation 611, an IMD layer 202 is formed over the second substrate 201 as shown in FIG. 10K. In some embodiments, the IMD layer 202 includes oxide such as silicon oxide or other suitable materials. In some embodiments, the IMD layer 202 is disposed over the first surface 201a of the second substrate 201. In some embodiments, an conductive structure 203 is disposed within the IMD layer 202. In some embodiments, the conductive structure 203 is electrically connected with the components or circuitries in the second substrate 201. In some embodiments, the conductive structure 203 includes tungsten, copper, aluminum, etc. In some embodiments, a dielectric layer 208 is disposed over the IMD layer 202. In some embodiments, the dielectric layer 208 includes oxide or other suitable dielectric materials.

Figures 1, 10L:
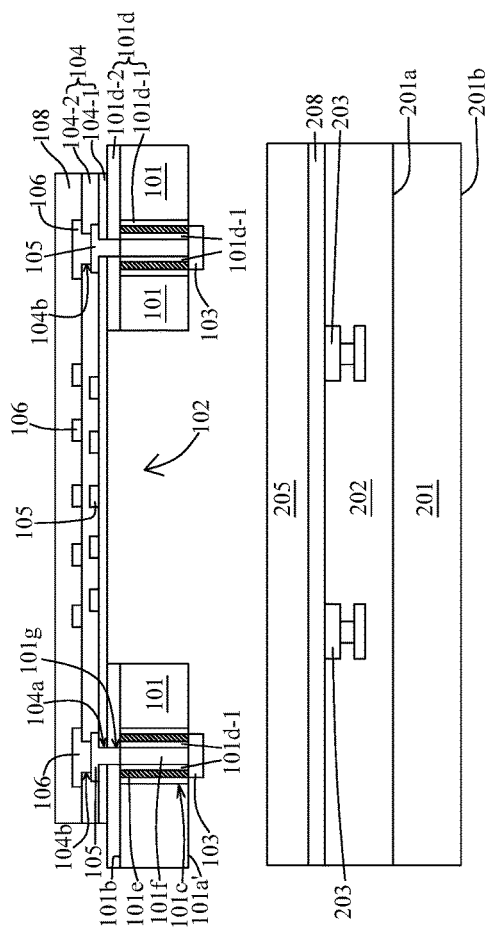
Figures 2, 10L:
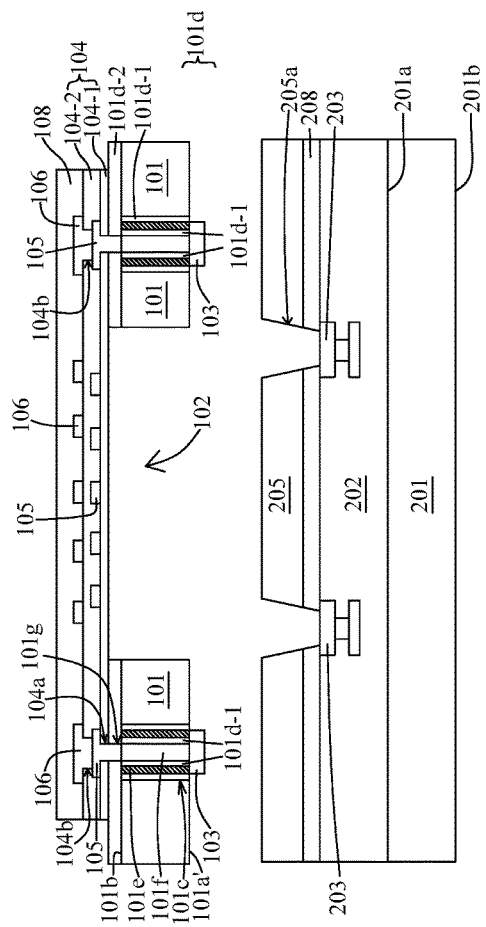

In operation 612, an isolation layer 205 is disposed and patterned as shown in FIGS. 10L-1 and 10L-2. In some embodiments, the isolation layer 205 is disposed over the second substrate 201. In some embodiments, the isolation layer 205 is attached to the IMD layer 202 by bonding operations. In some embodiments, the isolation layer 205 is a silicon substrate or silicon wafer. In some embodiments, the isolation layer 205 is bonded over the second substrate 201 by wafer bonding operations. In some embodiments, the isolation layer 205 includes dielectric material such as silicon oxide, silicon nitride, etc. In some embodiments, the isolation layer 205 is a passivation. In some embodiments, the isolation layer 205 is disposed by CVD or other suitable operations. In some embodiments, the dielectric layer 208 is patterned by removing some of the dielectric layer 208 disposed over the conductive structure 203. In some embodiments, the isolation layer 205 is patterned by removing some of the isolation layer 205 disposed over the conductive structure 203. In some embodiments, some of the isolation layer 205 are removed by photolithography and etching operations. As such, several fourth recesses 205a are formed after patterning the isolation layer 205 and the dielectric layer 208. In some embodiments, some of the isolation layer 205 are removed so as to reduce a thickness of the isolation layer 205. In some embodiments, the thickness of the isolation layer 205 is reduced from about 700 um to about 30 um-300 um after bonding over the second substrate 201.

Figure 10M:
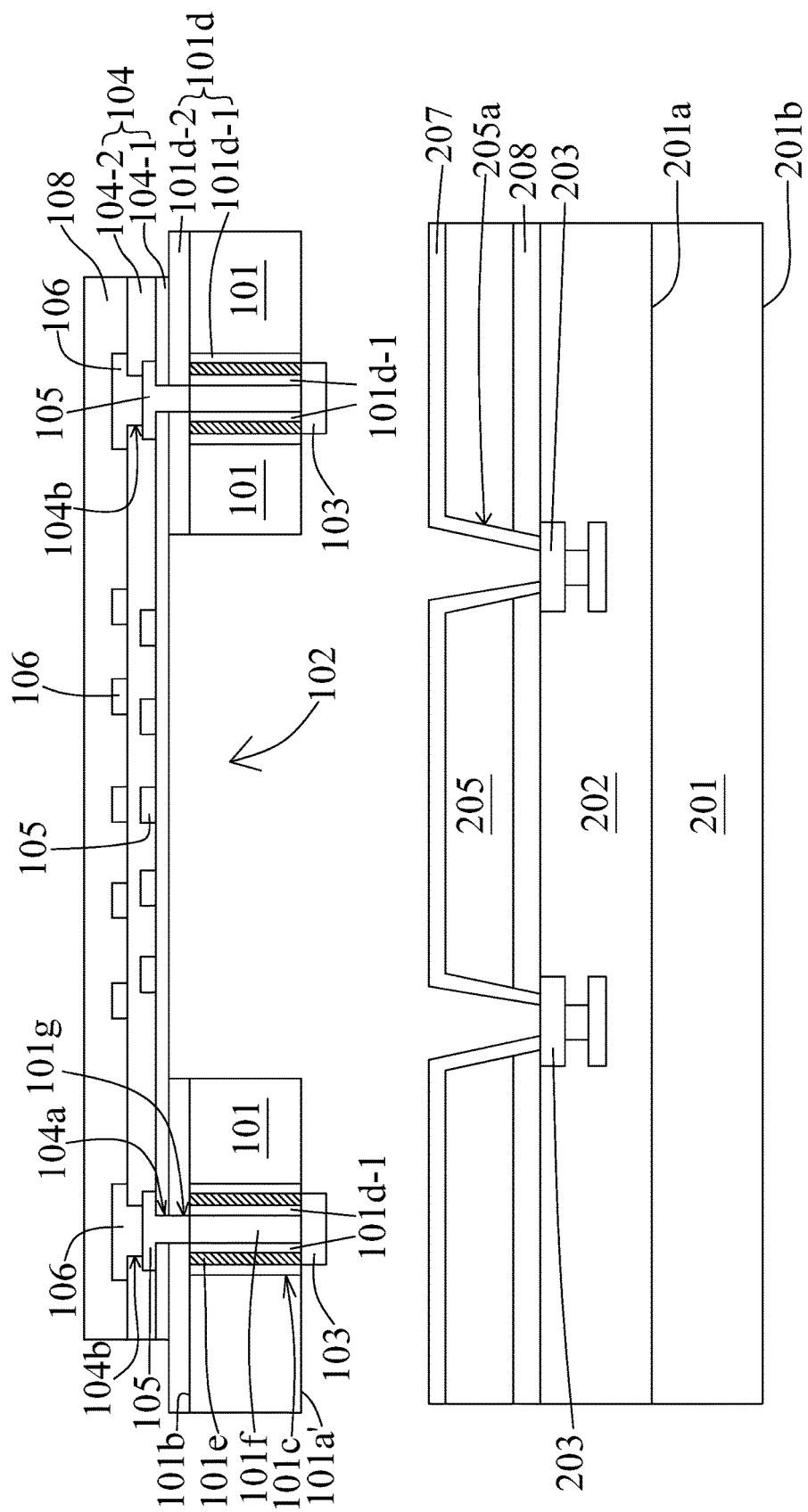
FIG. 10M is a cross-sectional view of a second substrate with a third oxide layer in accordance with some embodiments of the present disclosure.

In operation 613, a third oxide layer 207 is disposed as shown in FIG. 10M. In some embodiments, the third oxide layer 207 is disposed conformal to the isolation layer 205. In some embodiments, the third oxide layer 207 is disposed conformal to the fourth recesses 205a. In some embodiments, some of the third oxide layer 207 are disposed over the conductive structure 203, and then are removed to expose the conductive structure 203 by etching or other suitable operations. In some embodiments, the third oxide layer 207 includes silicon oxide or other suitable materials. In some embodiments, the third oxide layer 207 is disposed by CVD or other suitable operations.

Figure 10N:
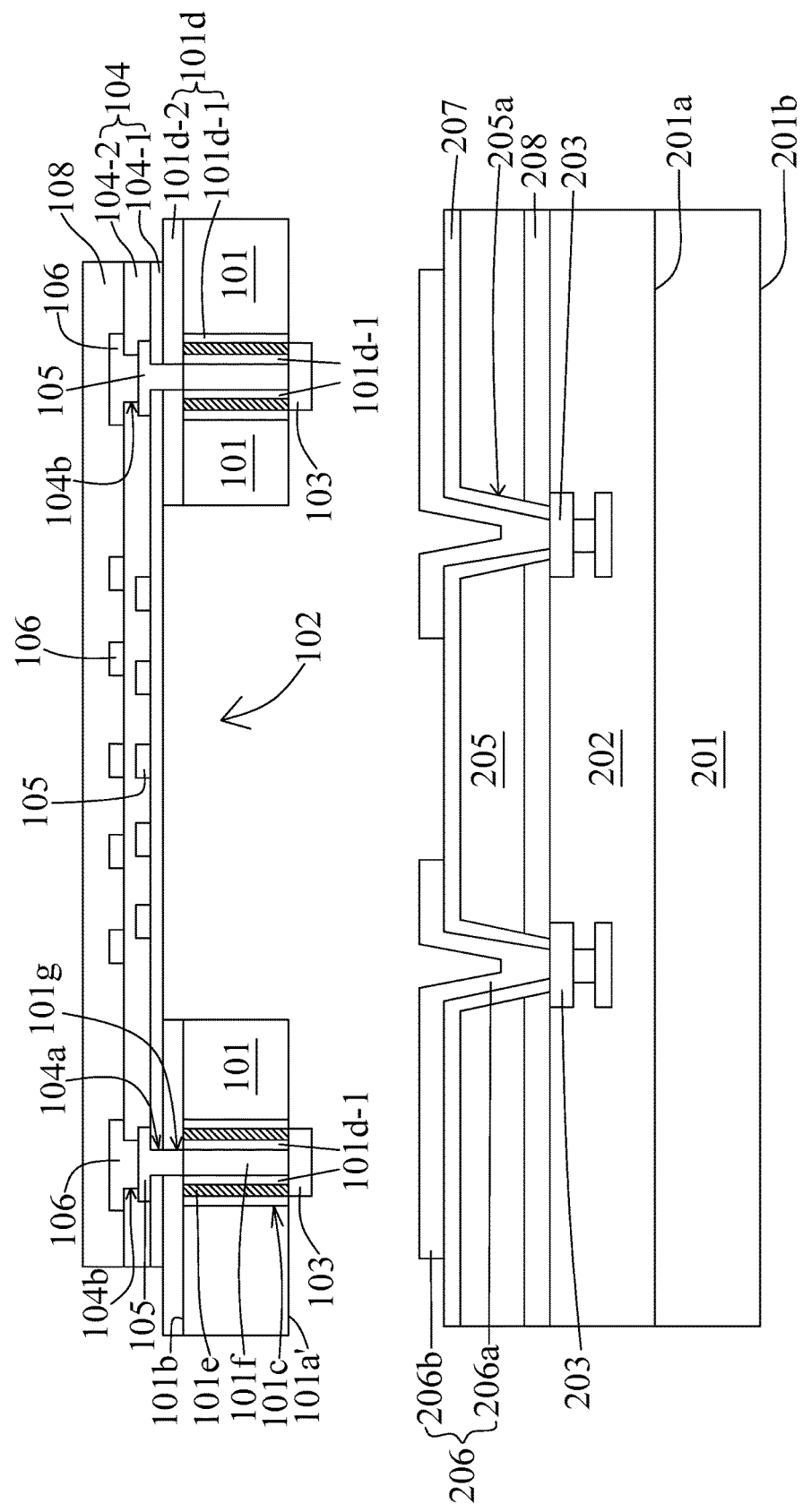
FIG. 10N is a cross-sectional view of a second substrate with an interconnect structure in accordance with some embodiments of the present disclosure.

In operation 614, an interconnect structure 206 is formed as shown in FIG. 10N. In some embodiments, the interconnect structure 206 is formed including formation of an via portion 206a and an elongated portion 206b. In some embodiments, the interconnect structure 206 is formed by electroplating, sputtering or other suitable operations. In some embodiments, the interconnect structure 206 includes conductive material such as aluminum, copper, etc. In some embodiments, the interconnect structure 206 is a redistribution layer (RDL).

In some embodiments, the via portion 206a contacts with the IMD layer 202. In some embodiments, the via portion 206a is disposed within the fourth recess 205a and electrically coupled with the conductive structure 203. In some embodiments, the elongated portion 206b is disposed along the third oxide layer 207. In some embodiments, the elongated portion 206b is electrically connected with the conductive structure 203 through the via portion 206a.

Figure 10O:
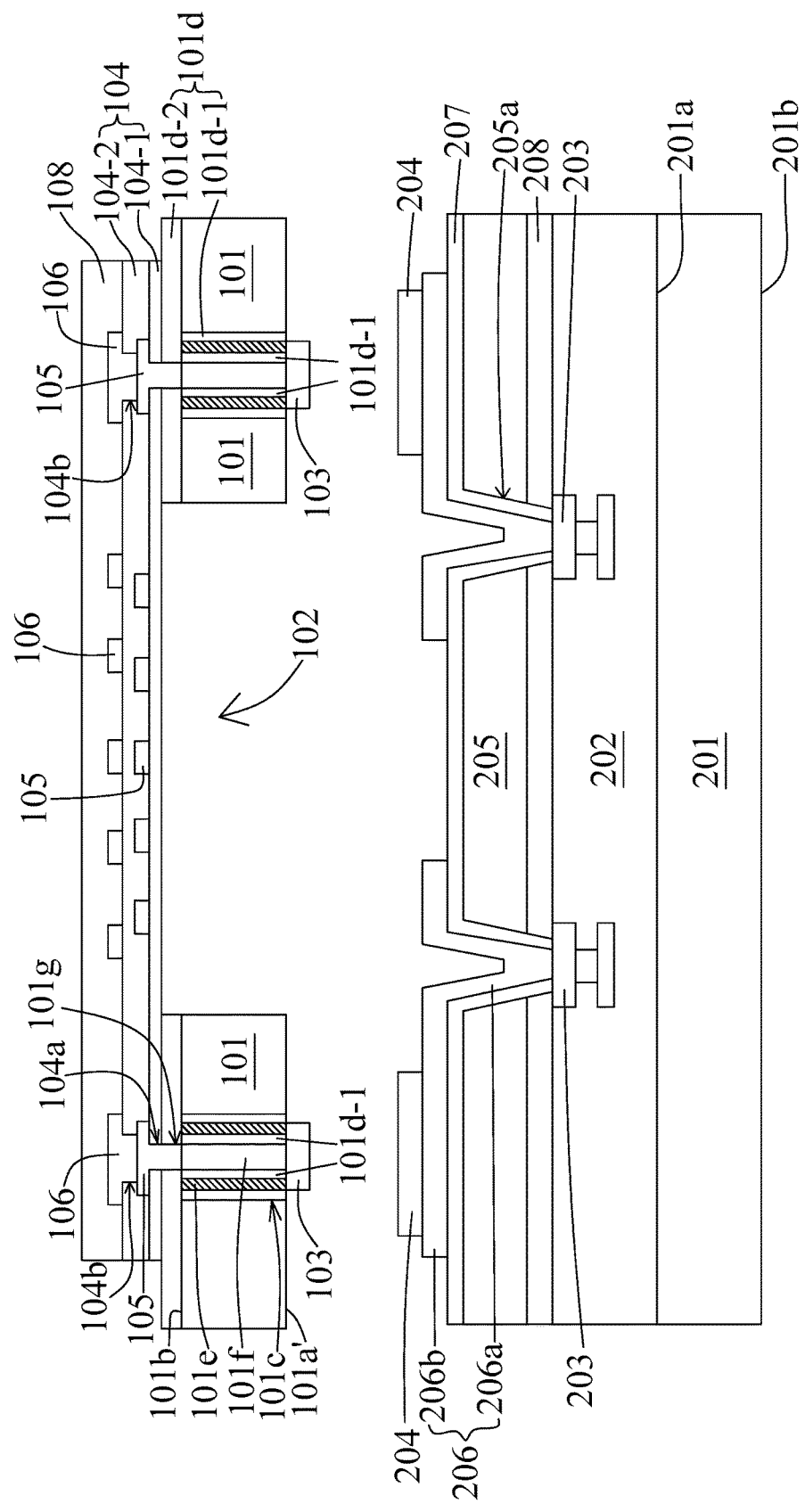
FIG. 10O is a cross-sectional view of a second substrate with a bonding structure in accordance with some embodiments of the present disclosure.

In operation 615, a bonding structure 204 is disposed over the elongated portion 206b of the interconnect structure 206 as shown in FIG. 10O. In some embodiments, the elongated portion 206b is configured to receive the bonding structure 204. The bonding structure 204 is disposed over the elongated portion 206b, so that the interconnect structure 206 is electrically connected with the bonding structure 204. In some embodiments, the bonding structure 204 is disposed by electroplating, sputtering or other suitable operations. In some embodiments, the bonding structure 204 includes germanium.

Figure 10P:
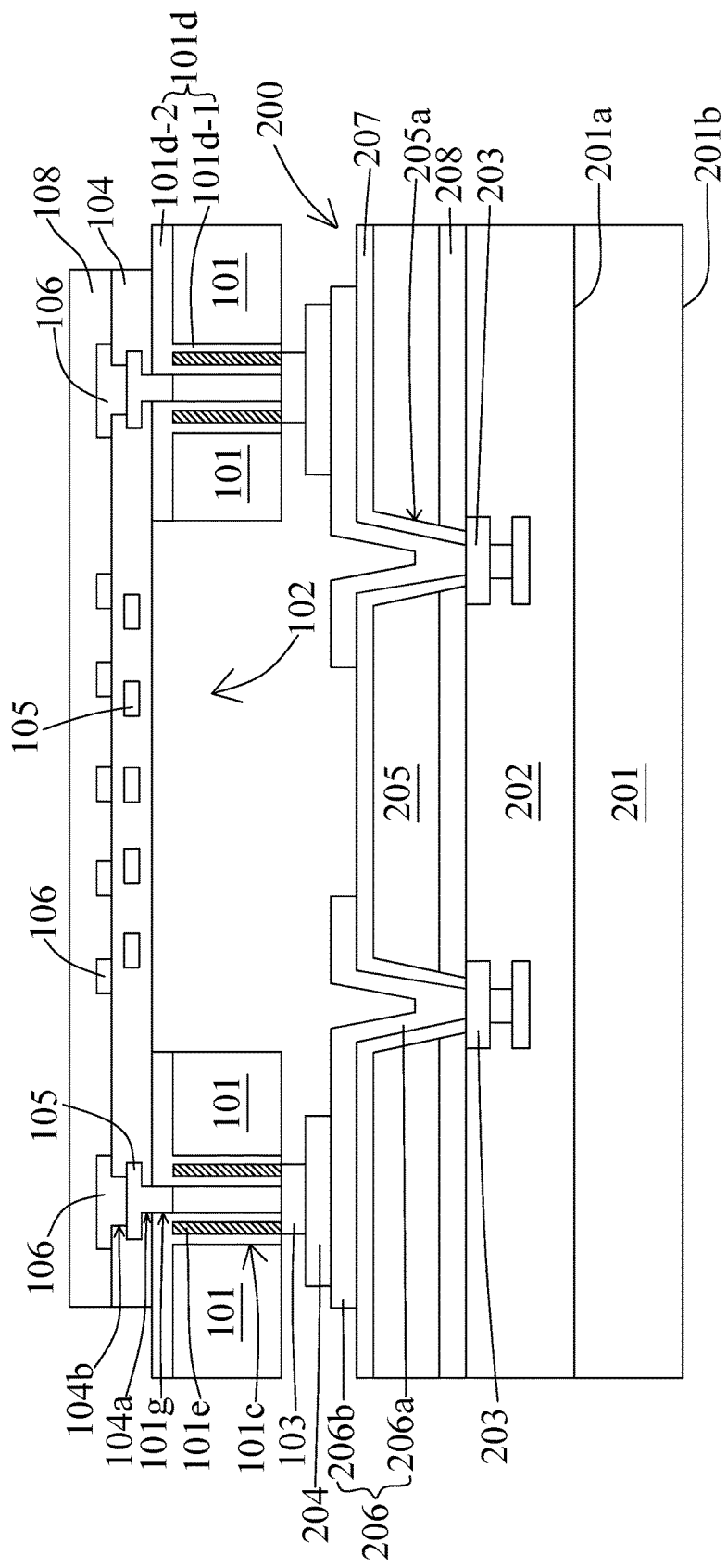
FIG. 10P is a cross-sectional view of a metallic material bonded with a bonding structure in accordance with some embodiments of the present disclosure.
Figure 10Q:
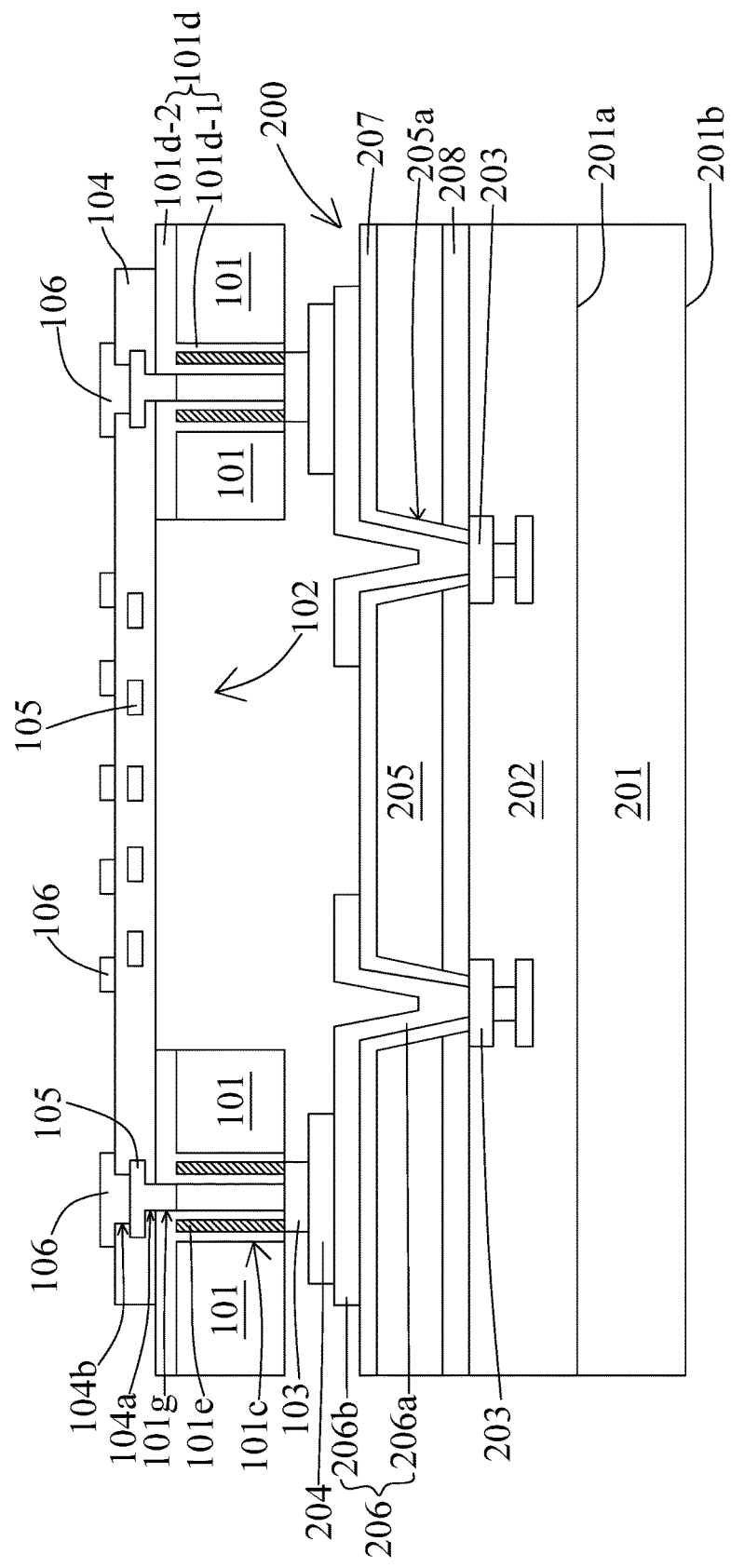
FIG. 10Q is a cross-sectional view of removal of a sacrificial oxide in accordance with some embodiments of the present disclosure.
Figure 10R:
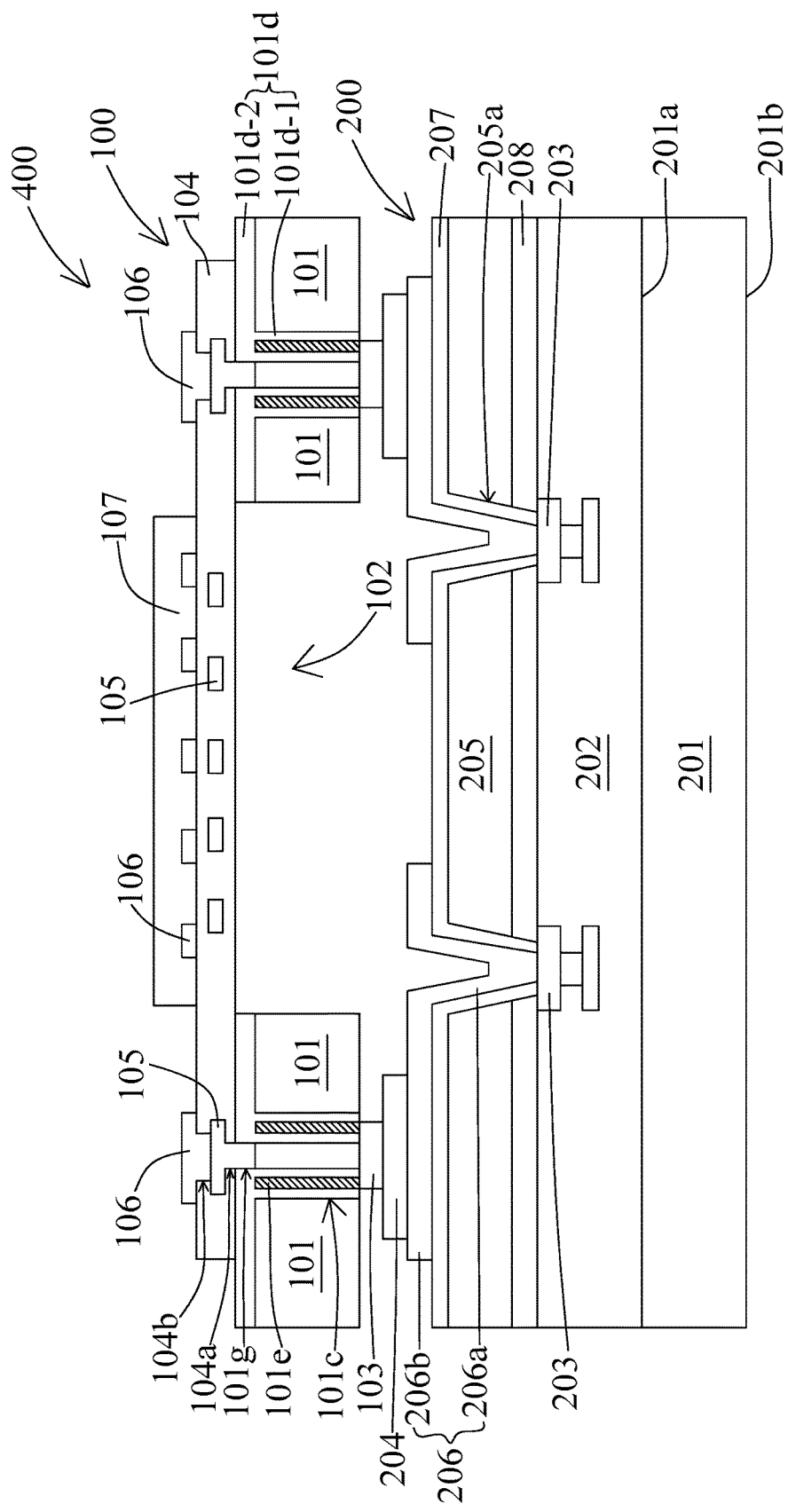
FIG. 10R is a cross-sectional view of a semiconductor structure in accordance with some embodiments of the present disclosure.

In operation 616, the metallic material 103 is bonded with the bonding structure 204 as shown in FIG. 10P. The operation 616 is similar to the operation 511 in FIG. 9K. In operation 617, the sacrificial oxide 108 is removed as shown in FIG. 10Q. The operation 617 is similar to the operation 512 in FIG. 9L. In operation 618, a sensing material 107 is disposed as shown in FIG. 10R. The operation 618 is similar to the operation 513 in FIG. 9M. In some embodiments, a semiconductor structure 400 including a first device 100 and second device 200 is formed. The semiconductor structure 400, the first device 100 and the second device 200 have similar configuration as in any one of FIGS. 7-8.

In the present disclosure, an improved semiconductor structure is disclosed. The semiconductor structure includes a MEMS device integrated with a CMOS device by formation of vias and bonding operations. Several vias are formed in a MEMS substrate, and a metallic material is disposed over a surface of the MEMS substrate. The metallic material is configured to be bonded with a bonding structure disposed over the CMOS substrate. As such, the MEMS device is integrated with the CMOS device by the metallic material and the bonding structure. Such integration can reduce a form factor of the semiconductor structure and enhance a performance of the semiconductor structure.

In some embodiments, a semiconductor structure includes a substrate including a plurality of vias passing through the substrate and filled with a conductive or semiconductive material, and an oxide layer surrounding the conductive or semiconductive material, the substrate defining a cavity therein; a membrane disposed over the substrate and the cavity; a heater disposed within the membrane and electrically connected with the substrate; and a sensing electrode disposed over the membrane and the heater.

In some embodiments, a portion of the substrate is surrounded by two or more of the plurality of vias. In some embodiments, the heater is disposed over the portion of the substrate. In some embodiments, the oxide layer is disposed between the substrate and the membrane. In some embodiments, the heater is extended laterally or vertically along the membrane. In some embodiments, the heater includes tungsten alloy, tungsten silicide (WSi), titanium tungsten (TiW), titanium aluminum nitride (TiAlN), tantalum aluminum (TaAl), chromium (Cr), platinum (Pt), titanium nitride (TiN), molybdenum (Mo), polysilicon, silicon carbide (SiC), tantalum nitride (TaN) or tantalum oxide (TaO). In some embodiments, the conductive or semiconductive material includes polysilicon. In some embodiments, the membrane includes silicon, silicon dioxide ($SiO_2$) or silicon nitride (SiN), silicon carbide (SiC), porous silicon or composite film. In some embodiments, the sensing electrode includes tungsten alloy, titanium tungsten (TiW), titanium aluminum nitride (TiAlN), tantalum aluminum (TaAl), titanium, titanium nitride (TiN), tantalum, tantalum nitride (TaN), tantalum oxide (TaO), platinum (Pt) or tantalum silicon nitride (TaSiN).

In some embodiments, a semiconductor structure includes a MEMS substrate including a first surface and a second surface opposite to the first surface, the MEMS substrate defining a cavity therein; a metallic material disposed over the first surface; a polysilicon disposed within the MEMS substrate; an oxide layer disposed between the polysilicon and the MEMS substrate; a membrane disposed over the second surface of the MEMS substrate and the cavity; a heater disposed within the membrane and electrically connected with the MEMS substrate; and a sensing electrode disposed over the membrane and the heater, and electrically connected with the MEMS substrate.

In some embodiments, the polysilicon is extended through the MEMS substrate the polysilicon is isolated from the substrate by the oxide layer. In some embodiments, the metallic material is disposed over the polysilicon. In some embodiments, the semiconductor structure further includes a CMOS substrate facing to the first surface of the MEMS substrate and electrically connected to the MEMS substrate through the metallic material. In some embodiments, the metallic material includes aluminum or copper.

In some embodiments, a method of manufacturing a semiconductor structure includes receiving a first substrate including a first surface, a second surface opposite to the first surface, a plurality of vias extending from the second surface towards the first surface and filled with a conductive or semiconductive material, a first oxide layer disposed between the first substrate and the conductive or semiconductive material, and a second oxide layer disposed over the first surface and the second surface of the first substrate; disposing and patterning a first membrane layer over the second oxide layer and the second surface; disposing and patterning a heater over the first membrane layer; disposing and patterning a second membrane layer over the heater and the first membrane layer; disposing a sensing electrode over the second membrane layer; disposing a sacrificial oxide over the sensing electrode and the second membrane layer; removing some of the first substrate from the first surface to expose the conductive or semiconductive material; forming a cavity surrounded by the first substrate; and removing the sacrificial oxide.

In some embodiments, the removing some of the first substrate includes grinding the first surface towards the second surface. In some embodiments, the method further includes disposing a metallic material over the first surface and the plurality of vias; disposing a sensing material over the sensing electrode; receiving a second substrate including a bonding structure disposed over the second substrate; bonding the metallic material with the bonding structure. In some embodiments, the bonding the metallic material with the bonding structure includes eutectic bonding operations. In some embodiments, the plurality of vias are formed by photolithography and etching operations, or the conductive or semiconductive material is disposed by CVD operations, or the first oxide layer and the second oxide layer are disposed by thermal oxidation operations.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A semiconductor structure, comprising:
   a substrate including a plurality of vias passing through the substrate and filled with a conductive or semiconductive material, and an oxide layer surrounding the conductive or semiconductive material, the substrate defining a cavity therein;
   a membrane disposed over the substrate and the cavity;
   a heater disposed within the membrane and electrically connected with the substrate; and
   a sensing electrode disposed over the membrane and the heater.

2. The semiconductor structure of claim 1, wherein a portion of the substrate is surrounded by two or more of the plurality of vias.

3. The semiconductor structure of claim 2, wherein the heater is disposed over the portion of the substrate.

4. The semiconductor structure of claim 2, further comprising a metallic material disposed over a surface opposite to the membrane.

5. The semiconductor structure of claim 4, wherein the metallic material is electrically connected with the sensing electrode through the portion of the substrate.

6. The semiconductor structure of claim 2, wherein the portion of the substrate is surrounded by the oxide layer.

7. The semiconductor structure of claim 1, wherein the oxide layer is disposed between the substrate and the membrane.

8. The semiconductor structure of claim 1, wherein the heater is extended laterally or vertically along the membrane.

9. The semiconductor structure of claim 1, wherein the heater includes tungsten alloy, tungsten silicide (WSi), titanium tungsten (TiW), titanium aluminum nitride (TiAlN), tantalum aluminum (TaAl), chromium (Cr), platinum (Pt), titanium nitride (TiN), molybdenum (Mo), polysilicon, silicon carbide (SiC), tantalum nitride (TaN) or tantalum oxide (TaO).

10. The semiconductor structure of claim 1, wherein the conductive or semiconductive material includes polysilicon.

11. The semiconductor structure of claim 1, wherein the membrane includes silicon, silicon dioxide ($SiO_2$) or silicon nitride (SiN), silicon carbide (SiC), porous silicon or composite film.

12. The semiconductor structure of claim 1, wherein the sensing electrode includes tungsten alloy, titanium tungsten (TiW), titanium aluminum nitride (TiAlN), tantalum aluminum (TaAl), titanium, titanium nitride (TiN), tantalum, tantalum nitride (TaN), tantalum oxide (TaO), platinum (Pt) or tantalum silicon nitride (TaSiN).

13. The semiconductor structure of claim 1, wherein a portion of the sensing electrode is coupled with a portion of the heater.

14. The semiconductor structure of claim 1, further comprising a sensing material disposed over the cavity and contacting with the sensing electrode.

15. A semiconductor structure, comprising:
a MEMS substrate including a first surface and a second surface opposite to the first surface, the MEMS substrate defining a cavity therein;
a metallic material disposed over the first surface;
a polysilicon disposed within the MEMS substrate;
an oxide layer disposed between the polysilicon and the MEMS substrate;
a membrane disposed over the second surface of the MEMS substrate and the cavity;
a heater disposed within the membrane and electrically connected with the MEMS substrate; and
a sensing electrode disposed over the membrane and the heater, and electrically connected with the MEMS substrate.

16. The semiconductor structure of claim 15, wherein the polysilicon is extended through the MEMS substrate.

17. The semiconductor structure of claim 15, wherein the polysilicon is isolated from the substrate by the oxide layer.

18. The semiconductor structure of claim 15, wherein the metallic material is disposed over the polysilicon.

19. The semiconductor structure of claim 15, further comprising a CMOS substrate facing to the first surface of the MEMS substrate and electrically connected to the MEMS substrate through the metallic material.

20. The semiconductor structure of claim 15, wherein the metallic material includes aluminum or copper.

* * * * *